(12) United States Patent
Endo et al.

(10) Patent No.: US 8,465,913 B2
(45) Date of Patent: *Jun. 18, 2013

(54) MITOCHONDRIAL FUNCTION OF PROHIBITIN 2 (PHB2)

(75) Inventors: Hitoshi Endo, Shimotsuke (JP); Katsumi Kasashima, Shimotsuke (JP)

(73) Assignee: Jichi Medical University, Shimotsuke-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/402,933

(22) Filed: Feb. 23, 2012

(65) Prior Publication Data

US 2012/0196298 A1    Aug. 2, 2012

Related U.S. Application Data

(62) Division of application No. 12/094,787, filed as application No. PCT/JP2006/323379 on Nov. 16, 2006, now Pat. No. 8,153,362.

(30) Foreign Application Priority Data

Nov. 24, 2005   (JP) ................................ 2005-339354

(51) Int. Cl.
  *C12Q 1/68*   (2006.01)
(52) U.S. Cl.
  USPC ................................ 435/6; 435/325; 435/375
(58) Field of Classification Search
  None
  See application file for complete search history.

(56) References Cited

PUBLICATIONS

Coates, P.J. et al., "Mammalian Prohibition Proteins Respond to Mitochondrial Stress and Decrease during Cellular Senescene", Experimental Cell Research, vol. 265, No. 2, pp. 262-273, (2001).
Tatsuta, T. et al., "Formation of Membrane-bound Ring Complexes by Prohibitins in Mitochondria", Molecular Biology of the Cell, vol. 16, pp. 248-259, (2005).
Coates, P.J. et al., "The Prohibitin Family of Mitochondrial Proteins Regulate Replicative Lifespan", Current Biology, vol. 7, No. 8, pp. 607-610, (1997).
Kurtev, V. et al., "Transcriptional Regulation by the Repressor of Estrogen Receptor Activity via Recruitment of Histone Deacetylases", The Journal of Biological Chemistry, vol. 279, No. 23, pp. 24834-24843, (2004).
Kasashima, K et al., "Mitochondrial Functions and Estrogen Receptor-dependent Nuclear Translocation of Pleiotropic Human Prohibitin 2", Journal Biological Chemistry, vol. 281, No. 47, pp. 36401-36410, (2006).
Kasashima, K et al., ERalpha-dependent nuclear Translocation of Mitochondrial Prohibitin 2, 20th IUBMB International Congress of Biochemistry and Molecular Biology and 11th FAOBMB Congress, p. 286, 5P-C-202, (2006).
U.S. Appl. No. 13/402,955, filed Feb. 23, 2012, Endo, et al.

*Primary Examiner* — Kimberly Chong
(74) *Attorney, Agent, or Firm* — Oblon, Spivak, McClelland, Maier & Neustadt, L.L.P.

(57) ABSTRACT

The present invention relates to a PHB2 gene regulator and a therapeutic drug for mitochondrial-function-related disease containing the same, for example.

2 Claims, 15 Drawing Sheets
(11 of 15 Drawing Sheet(s) Filed in Color)

| Band | Abbreviation | Accession Number | Name |
|------|--------------|------------------|------|
| I: | VDAC2 | P45880 | Voltage-dependent anion channel 2 |
| II: | Hax-1 | NP_006109 | HS1-associated protein X-1 |
| III: | PHB1 | NP_002625 | Prohibitin 1 |
| IV: | ANT2 | NP_001143 | Adenine nucleotide translocator 2 |

SEQUENCE LISTING

```
<160> NUMBER OF SEQ ID NOS: 24

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 1
gaacccuggc uacaucaaa                                                  19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 2
cccuggcuac aucaaacuu                                                  19
```

-continued

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 3
guggaucugc uucuccagu                                                    19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 4
ccccucuugg auuaaggaa                                                    19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 5
gauucgagca gcccagaau                                                    19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 6
gacugaagac uagccccuu                                                    19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 7
gaaaugagcc uagucacca                                                    19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 8
agaccuacag auggugaau                                                    19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: siRNA

```
<400> SEQUENCE: 9
ccuacaggau gaaaguuuc                                                   19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 10
ggguaagaaa ugagccuag                                                   19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 11
ucguaucuau cucacagcu                                                   19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 12
augagccuag ucaccaaga                                                   19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 13
gaugcuugga gaagcacug                                                   19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 14
ccuugugcug aaccuacag                                                   19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 15
cagcggcaga aaauugugc                                                   19

<210> SEQ ID NO 16
<211> LENGTH: 19
```

-continued

```
<212> TYPE: RNA
<213> ORGANISM: Artificial Sequence
<220> FEATURE:
<223> OTHER INFORMATION: Description of Artificial Sequence: siRNA

<400> SEQUENCE: 16
uucuugguag aaaaagcaa                                                      19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 17
acuucgcaag auucgagca                                                      19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 18
guucaaugcc ucacagcug                                                      19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 19
ggaagacuga agacuagcc                                                      19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 20
ucuguguuca ccguggaag                                                      19

<210> SEQ ID NO 21
<211> LENGTH: 1416
<212> TYPE: DNA
<213> ORGANISM: Homo sapiens
<220> FEATURE:
<221> NAME/KEY: CDS
<222> LOCATION: (186)..(1085)

<400> SEQUENCE: 21
aagttcgggt ccgtagtggg ctaaggggga gggtttcaaa gggagcgcac ttccgctgcc          60
ctttctttcg ccagccttac gggcccgaac cctcgtgtga agggtgcagt acctaagccg         120
gagcggggta gaggcgggcc ggcaccccct tctgacctcc agtgccgccg gcctcaagat         180 cagac atg gcc cag aac ttg aag gac ttg gcg gga cgg ctg ccc gcc ggg         230
      Met Ala Gln Asn Leu Lys Asp Leu Ala Gly Arg Leu Pro Ala Gly
        1               5                   10                  15 ccc cgg ggc atg ggc acg gcc ctg aag ctg ttg ctg ggg gcc ggc gcc         278
Pro Arg Gly Met Gly Thr Ala Leu Lys Leu Leu Leu Gly Ala Gly Ala
```

-continued

```
                    20                  25                  30
gtg gcc tac ggt gtg cgc gaa tct gtg ttc acc gtg gaa ggc ggg cac     326
Val Ala Tyr Gly Val Arg Glu Ser Val Phe Thr Val Glu Gly Gly His
                    35                  40                  45 aga gcc atc ttc ttc aat cgg atc ggt gga gtg cag cag gac act atc     374
Arg Ala Ile Phe Phe Asn Arg Ile Gly Gly Val Gln Gln Asp Thr Ile
                50                  55                  60 ctg gcc gag ggc ctt cac ttc agg atc cct tgg ttc cag tac ccc att     422
Leu Ala Glu Gly Leu His Phe Arg Ile Pro Trp Phe Gln Tyr Pro Ile
            65                  70                  75 atc tat gac att cgg gcc aga cct cga aaa atc tcc tcc cct aca ggc     470
Ile Tyr Asp Ile Arg Ala Arg Pro Arg Lys Ile Ser Ser Pro Thr Gly
        80                  85                  90                  95 tcc aaa gac cta cag atg gtg aat atc tcc ctg cga gtg ttg tct cga     518
Ser Lys Asp Leu Gln Met Val Asn Ile Ser Leu Arg Val Leu Ser Arg
                    100                 105                 110 ccc aat gct cag gag ctt cct agc atg tac cag cgc cta ggg ctg gac     566
Pro Asn Ala Gln Glu Leu Pro Ser Met Tyr Gln Arg Leu Gly Leu Asp
                115                 120                 125 tac gag gaa cga gtg ttg ccg tcc att gtc aac gag gtg ctc aag agt     614
Tyr Glu Glu Arg Val Leu Pro Ser Ile Val Asn Glu Val Leu Lys Ser
            130                 135                 140 gtg gtg gcc aag ttc aat gcc tca cag ctg atc acc cag cgg gcc cag     662
Val Val Ala Lys Phe Asn Ala Ser Gln Leu Ile Thr Gln Arg Ala Gln
        145                 150                 155 gta tcc ctg ttg atc cgc cgg gag ctg aca gag agg gcc aag gac ttc     710
Val Ser Leu Leu Ile Arg Arg Glu Leu Thr Glu Arg Ala Lys Asp Phe
160                 165                 170                 175 agc ctc atc ctg gat gat gtg gcc atc aca gag ctg agc ttt agc cga     758
Ser Leu Ile Leu Asp Asp Val Ala Ile Thr Glu Leu Ser Phe Ser Arg
                    180                 185                 190 gag tac aca gct gct gta gaa gcc aaa caa gtg gcc cag cag gag gcc     806
Glu Tyr Thr Ala Ala Val Glu Ala Lys Gln Val Ala Gln Gln Glu Ala
                195                 200                 205 cag cgg gcc caa ttc ttg gta gaa aaa gca aag cag gaa cag cgg cag     854
Gln Arg Ala Gln Phe Leu Val Glu Lys Ala Lys Gln Glu Gln Arg Gln
            210                 215                 220 aaa att gtg cag gcc gag ggt gag gcc gag gct gcc aag atg ctt gga     902
Lys Ile Val Gln Ala Glu Gly Glu Ala Glu Ala Ala Lys Met Leu Gly
        225                 230                 235 gaa gca ctg agc aag aac cct ggc tac atc aaa ctt cgc aag att cga     950
Glu Ala Leu Ser Lys Asn Pro Gly Tyr Ile Lys Leu Arg Lys Ile Arg
240                 245                 250                 255 gca gcc cag aat atc tcc aag acg atc gcc aca tca cag aat cgt atc     998
Ala Ala Gln Asn Ile Ser Lys Thr Ile Ala Thr Ser Gln Asn Arg Ile
                    260                 265                 270 tat ctc aca gct gac aac ctt gtg ctg aac cta cag gat gaa agt ttc     1046
Tyr Leu Thr Ala Asp Asn Leu Val Leu Asn Leu Gln Asp Glu Ser Phe
                275                 280                 285 acc agg gga agt gac agc ctc atc aag ggt aag aaa tga gcctagtcac     1095
Thr Arg Gly Ser Asp Ser Leu Ile Lys Gly Lys Lys
            290                 295 caagaactcc accccagag gaagtggatc tgcttctcca gtttttgagg agccagccag   1155
gggtccagca cagccctacc ccgcccagt atcatgcgat ggtcccccac accggttccc   1215
tgaacccctc ttggattaag gaagactgaa gactagcccc ttttctggga aattactttc   1275
ctcctccctg tgttaactgg ggctgttggg gacagtgcgt gatttctcag tgatttccta   1335
cagtgttgtt ccctccctca aggctgggag gagataaaca ccaacccagg aattctcaat   1395
```
aaatttttat tacttaacct g 1416

<210> SEQ ID NO 22
<211> LENGTH: 299
<212> TYPE: PRT
<213> ORGANISM: Homo sapiens

<400> SEQUENCE: 22

```
Met Ala Gln Asn Leu Lys Asp Leu Ala Gly Arg Leu Pro Ala Gly Pro
 1               5                  10                  15

Arg Gly Met Gly Thr Ala Leu Lys Leu Leu Gly Ala Gly Ala Val
            20                  25                  30

Ala Tyr Gly Val Arg Glu Ser Val Phe Thr Val Glu Gly His Arg
        35                  40                  45

Ala Ile Phe Phe Asn Arg Ile Gly Gly Val Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
        115                 120                 125

Glu Glu Arg Val Leu Pro Ser Ile Val Asn Glu Val Leu Lys Ser Val
    130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Gln Gln Glu Ala Gln
        195                 200                 205

Arg Ala Gln Phe Leu Val Glu Lys Ala Lys Gln Glu Gln Arg Gln Lys
    210                 215                 220

Ile Val Gln Ala Glu Gly Glu Ala Glu Ala Lys Met Leu Gly Glu
225                 230                 235                 240

Ala Leu Ser Lys Asn Pro Gly Tyr Ile Lys Leu Arg Lys Ile Arg Ala
                245                 250                 255

Ala Gln Asn Ile Ser Lys Thr Ile Ala Thr Ser Gln Asn Arg Ile Tyr
            260                 265                 270

Leu Thr Ala Asp Asn Leu Val Leu Asn Leu Gln Asp Glu Ser Phe Thr
        275                 280                 285

Arg Gly Ser Asp Ser Leu Ile Lys Gly Lys Lys
    290                 295
```

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: siRNA

<400> SEQUENCE: 23
aacacagccu uccuucugcu c 21

```
<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: siRNA

<400> SEQUENCE: 24
ccagagagga caaugaucu                                              19
```

MITOCHONDRIAL FUNCTION OF PROHIBITIN 2 (PHB2)

CROSS-REFERENCE TO RELATED APPLICATIONS

This application is a divisional of U.S. Ser No. 12/094,787 filed Mar. 4, 2009, now U.S. Pat. No. 8,153,362, which was a National Stage application of PCT/JP2006/323379 filed Nov. 16, 2006.

TECHNICAL FIELD

The present invention relates to a method for screening for a PHB2 gene regulator, for example.

BACKGROUND ART

Mitochondria conduct many reactions in eukaryotes. In particular, ATP synthesis via electron transport chain is important for organisms. Most ATP in cells is supplied by mitochondria. Other reaction systems in mitochondria relate to the TCA cycle, the heme synthesis system, the β oxidation cycle for fatty acids, the cycle for amino acid metabolism, and the like. Moreover, functions for maintaining Ca homeostasis, an active oxygen production system, and transport systems for metabolites, ions, proteins, and the like are present in mitochondria. Hence, mitochondria are intracellular organelles playing important roles in catabolic action and anabolic action in eukaryotes.

One thousand (1000) to 1500 types of protein are inferred to be present in human mitochondria. Thirteen (13) types thereof are proteins that are encoded by mitochondrial DNA and are subunits in electron transport chains. The other proteins, accounting for about 99%, are encoded by nuclear DNA. These proteins translocate to mitochondria after protein synthesis in cytoplasm. According to proteomic analysis, approximately 544 types of protein among the proteins existing in human mitochondria have been identified (Reichert A S and Neupert W., "Trends in Genetics," 2004, Vol. 20, No. 11, p. 556-562). However, many unknown proteins are inferred to be present.

As described above, mitochondrial DNA encodes some subunits of complexes I, III, IV, and V in electron transport chains. Specifically, mutation in mitochondrial DNA causes dysfunction of electron transport chains. Examples of diseases relating to dysfunction of electron transport chains include MELAS, MERRF, cardiomyopathy, LHON, and Leigh encephalopathy. Nucleotide mutation in mitochondrial DNA has also been observed in early cancer of the liver, the prostate gland, the bladder, and the head and neck, primary lung cancer, and Barrett's esophagus (Verma M. et al., "Nature reviews cancer," 2003, Vol. 3, No. 10, p. 789-795).

Meanwhile, abnormalities in mitochondrial proteins encoded by nuclear DNA cause many diseases as shown below: for example, (i) Friedreich's ataxia is caused by an abnormality in frataxin protein involved in Fe-S protein biosynthesis in mitochondria; (ii) an abnormality in Deafness dystonia peptide 1 (DDP1), which is a factor involved in protein translocation to mitochondria, is involved in Mohr-Tranebjaerg syndrome; (iii) retinal atrophy exhibiting autosomal dominant inheritance is caused by an abnormality in an OPA1 protein that causes mitochondrial membrane fusion; (iv) an abnormality in Mfn2, which is another factor involved in mitochondrial membrane fusion, causes the development of Charcot-Marie-Tooth neuropathy type 2; and (v) furthermore, an abnormality in thymidine phosphorylase of mitochondria causes the development of MNGIE (mitochondrial neuro gastrointestinal encephalomyopathy) exhibiting autosomal recessive inheritance and causing serious gastrointestinal symptoms.

In addition to the above involvement, involvement of mitochondrial dysfunction in more general diseases has also been demonstrated. For example, abnormalities in sugar metabolism and lipid metabolism due to mitochondrial dysfunction cause obesity, diabetes, and the like. Furthermore, a decreased intracellular ATP level due to mitochondrial dysfunction is a major factor of the cause of diseases such as Parkinson's disease and Alzheimer's disease. In recent years, it has also been reported that in Alzheimer's disease, amyloid β protein, which is an accumulated substance, binds intracellularly to an ABAD protein, which is a mitochondrial protein, so as to interfere with mitochondrial functions (Lustbader, J. W. et al., "Science," 2004, Vol. 304, No. 5669, p. 448-452).

It is known that 0.4% to 4% oxygen to be consumed by mitochondria becomes active oxygen via electron transport chains. Such active oxygen is thought to damage DNA, proteins, and the like so as to cause cell injuries, decreased cell counts, and the like, thereby promoting hypofunction in cells or aging of individual organisms.

Furthermore, mitochondria are involved in apoptosis induction and the pathway is thought to be associated with cell growth and malignant transformation (canceration).

Therefore, it is extremely important to maintain normal mitochondrial functions and to control the functions successfully, not only for antiaging, but also for maintenance of the homeostasis of an individual organism's body.

Meanwhile, a protein called prohibitin (hereinafter, referred to as "PHB") has been isolated from a mammal for the first time as a cell growth-suppressing factor. PHB is a protein that is highly conserved in organisms from yeast to mammals. It is known that in the PHB protein, 2 types of protein (PHB1 and PHB2, having primary amino acid structures analogous to each other) are present, form a complex, and are localized in the mitochondrial inner membrane. Yeast PHB proteins have been revealed to exert chaperone-like functions responsible for cell cycle control and stabilization of newly synthesized mitochondrial proteins (Berger, K. H. and Yaffe, M. P., "Mol Cell Biol.," 1998, Vol. 18, No. 7, p. 4043-4052; Nijtmans, L. G. et al., "EMBO J.," 2000, Vol. 19, No. 11, p. 2444-2451; and Piper P. W. and Bringloe, D., "Meth Ageing Dev.," 2002, Vol. 123, No. 4, p. 287-295). Moreover, in *Caenorhabditis elegans*, involvement of PHB1 in aging and early development has been reported (Artal-Sanz M. et al., "J Biol Chem.," 2003, Vol. 278, No. 34, p. 32091-32099).

Meanwhile, in mammals, various functions of PHB1 and PHB2, such as transcriptional control, have been suggested; however, their physiological functions in mitochondria have not yet been revealed (Delage-Mourroux R. et al., "J Biol Chem.," 2000, Vol. 275, No. 46, p. 35848-35856; and Sun L. et al., "J Cell Sci.," 2004, Vol. 117, p. 3021-3029).

DISCLOSURE OF THE INVENTION

As described above, it is extremely important to maintain normal mitochondrial functions and control the functions successfully, not only for antiaging, but also for maintenance of the homeostasis of an individual organism's body.

In view of the above circumstances, an object of the present invention is to provide, for example, a method for screening for an agent for regulating mitochondrial functions.

As a result of intensive studies to achieve the above object, the present inventors have discovered that human PHB2 protein in mitochondria has an anti-apoptotic effect and functions to generate mitochondrial membrane potential and to maintain mitochondrial morphology. Thus, the present inventors have completed the present invention.

The present invention encompasses the following (1) to (24).

(1) A method for screening for a PHB2 gene regulator, comprising the steps of: causing cells expressing a PHB2 gene to come into contact with a candidate substance under culture; and determining that the candidate substance is a PHB2 gene regulator if PHB2 gene expression or a PHB2 protein function is regulated in the PHB2-gene-expressing cells caused to come into contact with the candidate substance, when the cells are compared with cells expressing the PHB2 gene in the absence of the candidate substance.

(2) The method according to (1), in which the PHB2 protein function is selected from the group consisting of an anti-apoptotic effect, generation of mitochondrial membrane potential, and maintenance of mitochondrial morphology.

(3) The method according to (1) or (2), in which the PHB2 protein function is the capability of the PHB2 protein to interact with a protein that is encoded by a gene selected from the group consisting of a VDAC2 gene, a Hax-1 gene, a PHB1 gene, an ANT2 gene, and an OPA1 gene.

(4) The method according to (3), in which the capability to interact is the capability to form a complex.

(5) The method according to (1) or (2), in which the PHB2 protein function is the nucleus-mitochondria translocation function of the PHB2 protein.

(6) The method according to (5), in which the cells expressing the PHB2 gene further express a nuclear receptor selected from the group consisting of ERα, PPARα, and PPARγ2.

(7) The method according to (6), in which the cells expressing the PHB2 gene are cultured in the presence of estradiol.

(8) A PHB2 gene regulator, which is obtained by the method according to any one of (1) to (7).

(9) A. PHB2 gene regulator, containing the following siRNA (a) or (b):
(a) siRNA consisting of the nucleotide sequence represented by any one of SEQ ID NOS: 1 to 20; and
(b) siRNA consisting of a nucleotide sequence derived from that of the siRNA according to (a) by deletion, substitution, or addition of one or several nucleotides and having activity to inhibit PHB2 gene expression.

(10) A PHB2 gene regulator, containing an antagonist or an agonist of a nuclear receptor selected from the group consisting of ERα, PPARα, and PPARγ2.

(11) The PHB2 gene regulator according to any one of (8) to (10), in which the PHB2 gene regulator is selected from the group consisting of an anti-apoptotic agent, an agent for regulating mitochondrial membrane potential, and an agent for regulating mitochondrial membrane morphology.

(12) A therapeutic drug for mitochondrial-function-related disease, containing the PHB2 gene regulator according to any one of (8) to (11).

(13) A method for detecting a mitochondrial-function-related disease, comprising the steps of: measuring PHB2 gene expression or a PHB2 protein function in a biological sample derived from a subject; and determining that the subject has or is suspected of having a mitochondrial-function-related disease using as an indicator the presence of an abnormality in PHB2 gene expression or the PHB2 protein function.

(14) The method according to (13), in which the PHB2 protein function is selected from the group consisting of an anti-apoptotic effect, generation of mitochondrial membrane potential, and maintenance of mitochondrial morphology.

(15) The method according to (13) or (14), in which the PHB2 protein function is the capability of the PHB2 protein to interact with a protein that is encoded by a gene selected from the group consisting of a VDAC2 gene, a Hax-1 gene, a PHB1 gene, an ANT2 gene, and an OPA1 gene.

(16) The method according to (15), in which the capability to interact is the capability to form a complex.

(17) The method according to (13) or (14), in which the PHB2 protein function is the nucleus-mitochondria translocation function of the PHB2 protein.

(18) A method for screening for an agent for regulating mitochondrial functions, comprising the steps of: causing cells capable of expressing a PHB2 gene but having mitochondrial dysfunction to come into contact with a candidate substance under culture; and determining that the candidate substance is an agent for regulating mitochondrial functions using as an indicator the recovery or normalization of mitochondrial functions as a result of regulation of PHB2 gene expression or the PHB2 protein function in the mitochondrially dysfunctional cells caused to come into contact with the candidate substance, when the cells are compared with mitochondrially dysfunctional cells in the absence of the candidate substance.

(19) The method according to (18), in which the PHB2 protein function is selected from the group consisting of an anti-apoptotic effect, generation of mitochondrial membrane potential, and maintenance of mitochondrial morphology.

(20) The method according to (18) or (19), in which the PHB2 protein function is the capability of the PHB2 protein to interact with a protein that is encoded by a gene selected from the group consisting of a VDAC2 gene, a Hax-1 gene, a PHB1 gene, an ANT2 gene, and an OPA1 gene.

(21) The method according to (20), in which the capability to interact is the capability to form a complex.

(22) The method according to (18) or (19), in which the PHB2 protein function is the nucleus-mitochondria translocation function of the PHB2 protein.

(23) The method according to (22), in which the mitochondrially dysfunctional cells further express a nuclear receptor selected from the group consisting of ERα, PPARα, and PPARγ2.

(24) The method according to (23), in which the mitochondrially dysfunctional cells are cultured in the presence of estradiol.

The present invention is explained in detail as follows.

Interaction factors of human PHB2 protein in mitochondria were searched by immunoprecipation analysis and mass spectrometry using purified mitochondrial fractions derived from HeLa cells. As a result, a mitochondrial protein Hax-1 having an anti-apoptotic effect (NCBI accession No: NP_006109) (Cilenti L. et al., J Biol Chem., 279: 50295-50301, 2004), a VDAC2 protein, which is a configuration factor of PTP (permeability transition pore) (Swiss-Prot accession No: P45880), an ANT2 protein (NCBI accession No: NP_001143), and a PHB1 protein (NCBI accession No: NP_002625) were identified as interaction factors. Furthermore, it was revealed by an in vitro binding experiment that the PHB2 protein directly interacts with the. Hax-1 protein. Furthermore, when HeLa cells were subjected to PHB2 knockdown using an RNA interference method, decreased expression levels of the PHB1 protein and the Hax-1 protein, reduced mitochondrial membrane potential, induction of caspase-dependent cell death, decreased levels of the OPA1 protein (NCBI accession No: NP_056375), which is a regulatory factor for mitochondrial membrane morphology, and mitochondrial fragmentation (change in mitochondrial morphology) were observed.

Meanwhile, Hax-1 knockdown was found to have no effect on the expression level of a PHB2 protein in Hax-1 knockdown cells, but it was found to induce apoptosis to a degree similar to that induced by PHB2 knockdown. Thus, it was thought that apoptosis induced by PHB2 knockdown specifically results from a decrease in the level of the Hax-1 protein. Moreover, regarding mitochondrial morphology, mitochondrial fragmentation could not be observed in Hax-1 knockdown cells.

Based on the above findings, it was demonstrated that the PHB2 protein is involved in (1) stabilization of the Hax-1 protein, which is an interaction factor in mitochondria, (2) an anti-apoptotic effect that is mediated by (1), (3) generation of mitochondrial membrane potential, which is thought to be mediated by binding to the VDAC2 protein and the ANT2 protein, which form a PTP complex, and (4) regulation of mitochondrial morphology mediated by the OPA1 protein.

Accordingly, in mitochondria, the PHB2 protein exhibits an effect of physically or physiologically interacting with the Hax-1 protein, the VDAC2 protein, the ANT2 protein, the PHB1 protein, the OPA1 protein, and the like. The PHB2 protein also has an anti-apoptotic effect, an effect of generating mitochondrial membrane potential, and an effect of maintaining mitochondrial morphology.

Meanwhile, the PHB2 protein has been reported to be present in the nucleus of mammals, to function for transcriptional repression, and to recruit histone deacetylase (HDAC) (J. Biol. Chem. 279 (23), 24834-24843 (2004)). Localization of the PHB2 protein in the nucleus in MCF-7 cells derived from human breast cancer has been reported (J. Biol. Chem. 279 (23), 24834-24843 (2004)). In the present application, a mechanism by which the PHB2 protein is localized in mitochondria and the nucleus has been revealed. In HeLa cells, unlike MCF-7 cells, the PHB2 protein is localized in mitochondria alone and is not localized in the nucleus. However, it was revealed that the PHB2 protein translocates from mitochondria to the nucleus in the presence of an estrogen receptor (hereinafter, referred to as "ER") in an estradiol-dependent manner (hereinafter, referred to as "E2"). A region required for the translocation of PHB2 to the nucleus is dependent on the carboxyl terminus of the PHB2 protein. Furthermore, a mitochondrial targeting signal and a weak transmembrane domain are present in the amino terminus of the PHB2 protein. This portion alone translocates to mitochondria. Translocation of PHB2 to the nucleus takes place also in the presence of PPARα, or PPARγ2, which is a non-ER nuclear receptor.

As described above, it was revealed in the present application that the PHB2 protein is a protein that is localized in both mitochondria and the nucleus and functions for generation of mitochondrial membrane potential, an anti-apoptotic effect, maintenance of mitochondrial morphology, and the like through transcriptional repression in the nucleus and stabilization of various proteins in mitochondria.

The present invention is described as follows based on the above-explained novel functions of the PHB2 protein.

The method for screening for a PHB2 gene regulator according to the present invention comprises: causing cells expressing a PHB2 gene to come into contact with a candidate substance under culture; and determining that the candidate substance is a PHB2 gene regulator if PHB2 gene expression or PHB2 protein functions are regulated in the PHB2-gene-expressing cells caused to come into contact with the candidate substance, when the cells are compared with PHB2-gene-expressing cells in the absence of the candidate substance.

A human PHB2 gene is DNA consisting of the nucleotide sequence of SEQ ID NO: 21, which has been registered with the NCBI under NCBI accession No: NM_007273. In addition, CDS is the nucleotide sequence between nucleotides 186 and 1085 in the nucleotide sequence of SEQ ID NO: 21. The human PHB2 protein is registered with the NCBI under NCBI accession No: NP_009204 and is a protein consisting of the amino acid sequence of SEQ ID NO: 22. Examples of PHB2 genes or PHB2 proteins derived from non-human organisms include PHB2_YEAST (swissprot: accession P50085) derived from *Saccharomyces cerevisiae*, PHB2_CAEEL (swissprot: accession P50093) derived from *Caenorhabditis elegans*, ATPHB2 (PROHIBITIN 2) [*Arabidopsis thaliana*] (NCBI accession No: NP_973755) derived from *Arabidopsis thaliana*, prohibitin 2 [*Xenopus tropicalis*] (NCBI accession No: NP_001016551) derived from *Xenopus tropicalis*, PHB2 MOUSE (swissprot: accession O35129) derived from a mouse, and PHB2 RAT (swissprot: accession Q5XIH7) derived from a rat. Examples of such PHB2 gene in the present invention include not only DNAs consisting of nucleotide sequences of the above SEQ ID NOS: or accession Nos. Furthermore, DNA consisting of a nucleotide sequence derived from that of the above DNA by deletion, substitution, or addition of 1 or a plurality of (e.g., 1 to 10 and preferably 1 to 5) nucleotides and encoding a protein having PHB2 protein functions is also included herein. Moreover, examples of such PHB2 gene also include DNAs each having 90% or more, preferably 95% or more, 97% or more, and more preferably 98% or more, and particularly preferably 99% or more identity with DNA consisting of the nucleotide sequence of the above SEQ ID NO: or accession No and encoding a protein having PHB2 protein functions. Alternatively, not only DNAs encoding the amino acid sequences of the above SEQ ID NOS: or accession Nos., but also DNAs each encoding a protein consisting of an amino acid sequence derived from the above amino acid sequence by deletion, substitution, or addition of 1 or a plurality of (e.g., 1 to 10 and preferably 1 to 5) amino acids and having PHB2 protein functions are also included in the examples of the PHB2 gene.

Here, examples of PHB2 protein functions include an anti-apoptotic effect, generation of mitochondrial membrane potential, maintenance of mitochondrial morphology, capability (e.g., the capability to form a complex, the capability for signal transduction, the capability for protein stabilization, protein conformation and/or, the capability for functional regulation (physiological interaction is also included herein)) of the PHB2 protein to interact with a protein that is encoded by a gene selected from the group consisting of the VDAC2 gene, the Hax-1 gene, the PHB1 gene, the ANT2, gene, and the OPA1 gene (hereinafter, the proteins are referred to as the VDAC2 protein, the Hax-1 protein, the PHB1 protein, the ANT2 protein, and the OPA1 protein, respectively), and a nucleus-mitochondria translocation function. "Capability to form a complex" in the description refers to the capability to form a complex that is formed via direct or indirect binding in mitochondria, nucleus, cytoplasm, and the like. Examples of components of such a complex include proteins or nucleic acids, or some types of lipid. Furthermore, "nucleus-mitochondria translocation function" refers to a function to translocate between mitochondria and the nucleus. Examples of such function include a function to translocate between mitochondria and cytoplasm and a function to translocate between cytoplasm and the nucleus. Furthermore, an example of such mechanism for nucleus-mitochondria translocation is a transport mechanism by which transporters that mediate such translocation or ligands that stimulate the same are included.

Cells expressing a PHB2 gene may be any cells, as long as they express the PHB2 gene. Examples of such cells include cells of human-derived cell lines, such as HeLa cells (derived from human cervical cancer), MCF-7 cells (derived from human breast cancer), U-2OS cells (derived from human osteosarcoma), and human fibroblasts. Examples of such cells further include B6.1 cells (derived from mouse myeloma), mouse embryonic stem cells, and SWISS 3T3 cells (derived from mouse fibroblasts). Furthermore, examples of PHB2-gene-expressing cells also include cells transfected with the above PHB2 gene (or in which the PHB2 gene has been overexpressed). For example, a PHB2 gene contained in a PCR product or a vector can be introduced into cells by an electroporation method, a calcium phosphate method, a lipofection method, or the like. An example of a method for confirming the expression of a PHB2 gene in PHB2-gene-expressing cells at the mRNA level is a method that involves confirming by RT-PCR, quantitative PCR, or Northern blotting using primers or a probe specific to the PHB2 gene. Moreover, at the protein level, PHB2 gene expression can be confirmed using an immunological method such as ELISA, flow cytometry, or Western blotting using an antibody specific to the PHB2 protein, for example.

In the meantime, in the present invention, examples of a candidate substance include nucleic acids, peptides, proteins, synthetic compounds, culture supernatants of microorganisms, natural ingredients derived from plants or marine organisms, plant extracts, and animal tissue extracts.

The method for screening for a PHB2 gene regulator according to the present invention comprises causing cells expressing a PHB2 gene to come into contact with a candidate substance under culture. Such PHB2-gene-expressing cells can be cultured by adequately selecting medium and culture conditions (e.g., temperature and pH) depending on each cell. Here, contact means the status that the candidate substance has an effect on cells expressing the PHB2 gene. For example, a candidate substance may be simply added to medium of PHB2-gene-expressing cells. Alternatively, a candidate substance may be embedded in or bound to a liposome and then added to medium. Furthermore, a candidate substance may be added together with a type of carrier substance (protein, lipid, or the like) to medium. Furthermore, a candidate substance may be directly introduced into PHB2-gene-expressing cells via microinjection or the like. The time for culturing may also be any time length as long as it is sufficient for a candidate substance to have an effect on PHB2-gene-expressing cells. Such time for culturing may range from 1 to 72 hours and preferably may range from 12 to 24 hours, for example.

Subsequently, the method for screening for a PHB2 gene regulator according to the present invention comprises determining whether or not PHB2 gene expression or PHB2 protein functions are regulated in the PHB2-gene-expressing cells caused to come into contact with the candidate substance, when the cells are compared with PHB2-gene-expressing cells in the absence of the candidate substance. Here, regulation of PHB2 gene expression means a decrease or an increase in PHB2 gene expression at the mRNA level or the protein level. Moreover, regulation of PHB2 protein functions means enhanced PHB2 protein functions described above.

In a method for evaluating the regulation of PHB2 gene expression, mRNA or a protein is extracted from cells expressing the PHB2 gene after culturing. Subsequently, a PHB2 gene expression level in the thus obtained mRNA or protein is compared with a PHB2 gene expression level in cells expressing the PHB2 gene cultured in the absence of the candidate substance. In addition, a PHB2 gene expression level at the mRNA level or protein level can be measured according to the above-described method.

It can be determined that a candidate substance is a PHB2 gene regulator: if PHB2 gene expression levels are significantly increased (e.g., 1.5- to 100-fold and preferably 2- to 5-fold) at the mRNA level or protein level in PHB2-gene-expressing cells caused to come into contact with the candidate substance; or if PHB2 gene expression levels are significantly decreased (e.g., decreased to $\frac{1}{2}$ to $\frac{1}{1000}$ and preferably $\frac{1}{4}$ to $\frac{1}{10}$), when the cells are compared with PHB2-gene-expressing cells cultured in the absence of a candidate substance.

Meanwhile, regulation of PHB2 protein functions can be evaluated separately according to each function.

The anti-apoptotic effect can be evaluated by detecting DNA fragmentation, cell membrane structural changes due to binding of Annexin V, disappearance of mitochondrial membrane potential, the activity of an apoptosis-associated enzyme, such as caspase, and/or transfer of cytochrome c from mitochondria to cytoplasm, for example.

Generation of mitochondrial membrane potential can be evaluated by subjecting PHB2-gene-expressing cells to staining using a mitochondria staining marker Rh123 depending on the mitochondrial membrane potential and then observing the degrees of staining under a microscope, for example.

Maintenance of mitochondrial morphology can be evaluated by subjecting PHB2-gene-expressing cells to staining of mitochondria using MitoTracker Red and then observing the mitochondrial morphology via microscopic observation, for example.

Moreover, the capability of the PHB2 protein to interact with the VDAC2 protein, the Hax-1 protein, the PHB1 protein, the ANT2 protein, or the OPA1 protein (e.g., capability to form a complex) can be evaluated by subjecting a protein derived from PHB2-gene-expressing cells to immunological analysis using an antibody specific to each protein and then observing association between the proteins, for example.

Furthermore, regarding the nucleus-mitochondria translocation function, translocation of a PHB2 protein from mitochondria to the nucleus can be evaluated by culturing PHB2-gene-expressing cells that express ERα, PPARα, or PPARγ2 (in the presence of E2 in the case of ERα) and then staining using an antibody specific to the PHB2 protein, for example. The amount of E2 to be added to medium ranges from $1 \times 10^{-12}$ to $1 \times 10^{-4}$ M and preferably ranges from $1 \times 10^{-7}$ to $1 \times 10^{-6}$ M, for example.

It can be determined that a candidate substance is a PHB2 gene regulator when the PHB2 protein functions were observed to be significantly enhanced (e.g., enhanced 1.5- to 100-fold and preferably 2- to 10-fold) in PHB2-gene-expressing cells caused to come into contact with the candidate substance, when the cells are compared with PHB2-gene-expressing cells cultured in the absence of the candidate substance.

Meanwhile, according to the above method for screening for a PHB2 gene regulator according to the present invention, an agent for regulating mitochondrial functions can be screened for. The method for screening for an agent for regulating mitochondrial functions according to the present invention comprises causing cells capable of expressing the PHB2 gene but having mitochondrial dysfunction to come into contact with a candidate substance under culture; and determining that the candidate substance is an agent for regulating mitochondrial functions using as an indicator the recovery or normalization of mitochondrial functions as a result of regulation of PHB2 gene expression or PHB2 protein functions in the mitochondrially dysfunctional cells caused to come into contact with the candidate substance, when the cells are compared with mitochondrially dysfunctional cells in the absence of the candidate substance.

Here, cells capable of expressing the PHB2 gene but having mitochondrial dysfunction (hereinafter, referred to as simply "mitochondrially dysfunctional cells") are cells expressing the PHB2 gene and having abnormalities in mitochondrial functions as described above. Examples of such cells include cells subjected to PHB2 knockdown and caused to express another mutant PHB2.

In the method for screening for an agent for regulating mitochondrial functions according to the present invention, according to the above method for screening for a PHB2 gene regulator according to the present invention, whether or not mitochondrial functions are recovered or normalized (as a result of regulation of PHB2 gene expression or PHB2 protein functions in mitochondrially dysfunctional cells caused to come into contact with candidate substances) is determined via comparison of the cells with mitochondrially dysfunctional cells in the absence of the candidate substances. Based on such indicator, an agent for regulating mitochondrial functions can be selected from among the above candidate substances.

Examples of the PHB2 gene regulator according to the present invention include a PHB2 gene regulator that is obtained by the above method for screening for a PHB2 gene regulator, a PHB2 gene regulator containing the following siRNA (a) or (b): (a) siRNA consisting of the nucleotide sequence represented by any one of SEQ ID NOS: 1 to 20; or (b) siRNA consisting of a nucleotide sequence derived from that of the siRNA of (a) above by deletion, substitution, or addition of one or several (e.g., 1 to 5 and preferably 1 to 3) nucleotides and having activity of inhibiting PHB2 gene expression, and a PHB2 gene regulator containing an antagonist or an agonist for an ERα, PPARα, or PPARγ2 nuclear receptor. Furthermore, siRNA having 90% or more, preferably 95% or more, 97% or more, more preferably 98% or more, and particularly preferably 99% or more identity with the siRNA of (a) above and having activity of inhibiting PHB2 gene expression can also be an example of the PHB2 gene regulator according to the present invention.

The siRNA (a) or (b) above can be chemically synthesized by a known method for nucleic acid synthesis, for example.

Examples of an antagonist or an agonist for an ERα, PPARα, or PPARγ2 nuclear receptor include antagonists of ER, such as ICI182,780, DDE, and Tamoxifen, agonists of ER, such as DES (Diethylstilbestrol), genistein, nonyl phenol, and bisphenol A, agonists of PPARα, such as WY-14643, ETYA, Benzafibrate, and LY171883, antagonists of PPARα, such as GW6471, agonists of PPARγ, such as GW9662 and Troglitazone, and antagonists of PPARγ, such as thiazolidinedione.

Further examples of the PHB2 gene regulator include agonists or antagonists of other nuclear receptors of TR, PR, RXR, and the like.

Furthermore, as a PHB2 gene regulator, a chimeric protein comprising a mitochondrial targeting signal and a transmembrane domain (in the human PHB1 protein, amino acid residues 1 to 50 from the N-terminus) of a PHB1 protein and the C-terminus of the PHB2 protein (in the human PHB2 protein, amino acid residues 51 to 299 from the N-terminus) can be used, for example.

In addition, based on PHB2 protein functions, the PHB2 gene regulator can be used as an anti-apoptotic agent, an agent for regulating mitochondrial membrane potential, or an agent for regulating the morphology of mitochondrial membrane.

The therapeutic drug for mitochondrial-function-related disease according to the present invention is characterized by containing the PHB2 gene regulator according to the present invention. Here, the mitochondrial-function-related disease means disease associated with mitochondrial dysfunction. Examples of such mitochondrial-function-related disease include obesity, diabetes, Parkinson's disease, Alzheimer's disease, and cancer (e.g., breast cancer), but are not limited thereto.

The therapeutic drug for mitochondrial-function-related disease according to the present invention may directly be the PHB2 gene regulator according to the present invention or may be a drug that is formulated into a dosage form (e.g., a tablet, a powder, an emulsion, or a capsule) using a generally employed solid or liquid carrier, emulsifying and dispersing agent, or the like. Examples of the above carrier include water, gelatin, starch, magnesium stearate, lactose, and plant oil. The content of the PHB2 gene regulator in the therapeutic drug for mitochondrial-function-related disease according to the present invention and the dosage of the therapeutic drug can be adequately varied depending on purposes of administration, routes of administration, dosage forms, and the like.

Pharmacological evaluation of the therapeutic drug for mitochondrial-function-related disease according to the present invention can be performed, for example, at the in vitro level using the above-described mitochondrially dysfunctional cells or at the in vivo level using animal models for mitochondrial-function-related disease such as Alzheimer's disease. For example, pharmacological evaluation can be performed based on whether or not mitochondrial dysfunction is restored or normalized in mitochondrially dysfunctional cells cultured in the presence of the therapeutic drug for mitochondrial-function-related disease according to the present invention, when the cells are compared with cells in the absence of the therapeutic drug. Alternatively, pharmacological evaluation can also be performed based on whether or not a mitochondrial-function-related disease can be treated or ameliorated in a mitochondrial-function-related disease animal model to which the therapeutic drug for mitochondrial-function-related disease according to the present invention has been administered, when the animal model is compared with an animal model to which no such therapeutic drug has been administered.

The method for detecting a mitochondrial-function-related disease according to the present invention comprises: measuring PHB2 gene expression or PHB2 protein functions in a biological sample derived from a subject; and determining that the subject has or is suspected of having a mitochondrial-function-related disease using as an indicator the presence of an abnormality in PHB2 gene expression or PHB2 protein functions.

Examples of a biological sample include subject-derived cells such as fibroblasts, myoblasts, white blood cells, spermatids, and egg cells, tissues and organs containing these cells, body fluids such as blood and saliva, and excretory substances.

The method for detecting a mitochondrial-function-related disease according to the present invention can be performed according to the above method for screening for a PHB2 gene regulator according to the present invention. Specifically, first, PHB2 gene expression or PHB2 protein functions in cells in a biological sample are measured. Subsequently, whether or not PHB2 gene expression or PHB2 protein functions are abnormal is determined via comparison with cells derived from a normal subject. Here, the abnormality in PHB2 gene expression or PHB2 protein functions means an increase or a decrease in PHB2 gene expression or a decrease in PHB2 protein functions, for example. When an abnormality is found in PHB2 gene expression or PHB2 protein functions, it can be determined that the subject from which the biological sample is derived has or is suspected of having a mitochondrial-function-related disease.

As explained above, based on the novel functions of the PHB2 protein, a PHB2 gene regulator can be identified and an agent for regulating mitochondrial functions or a therapeutic drug for mitochondrial-function-related disease can be provided.

This specification includes the contents as disclosed in the specification and/or drawings of Japanese Patent Application No. 2005-339354, which is a priority document of the present application.

BRIEF DESCRIPTION OF THE DRAWINGS

The patent or application file contains at least one drawing executed in color. Copies of this patent or patent application publication with color drawing(s) will be provided by the office upon request and payment of the necessary fee.

BEST MODES FOR CARRYING OUT THE INVENTION

EXAMPLES

Hereafter, the present invention is described in greater detail with reference to the following examples, although the technical scope of the present invention is not limited thereto.

In addition, proteins mentioned in these Examples were all derived from human, except for proteins (e.g., FLAG tag, GST, GFP, and luciferase) used as labels or reporters.

Example 1

Intracellular Localization of PHB1 Protein or PHB2 Protein in HeLa Cell

A gene encoding a PHB1 protein (hereinafter, referred to as "PHB1-FLAG") or a PHB2 protein (hereinafter, referred to as "PHB2-FLAG"), in which a FLAG tag had been fused to the carboxyl terminus, was expressed transiently in HeLa cells (derived from human cervical cancer).

The method employed herein is as follows. cDNA encoding PHB1-FLAG or PHB2-FLAG was inserted into a mammalian cell expression vector pCMV-SPORT and then HeLa cells were transfected with the vector. After approximately 12 hours, these cells were fixed and then subjected to immunostaining. Antibodies used herein are as follows: an anti-FLAG rabbit polyclonal antibody and an anti-cytochrome C (cyt.c) mouse monoclonal antibody as a control antibody for staining mitochondria were used as primary antibodies; and as secondary antibodies, an Alexa488-labeled anti-rabbit antibody and a Cy3-labeled anti-mouse antibody were used. These cells were observed under a confocal laser scanning microscope.

Figure 1:
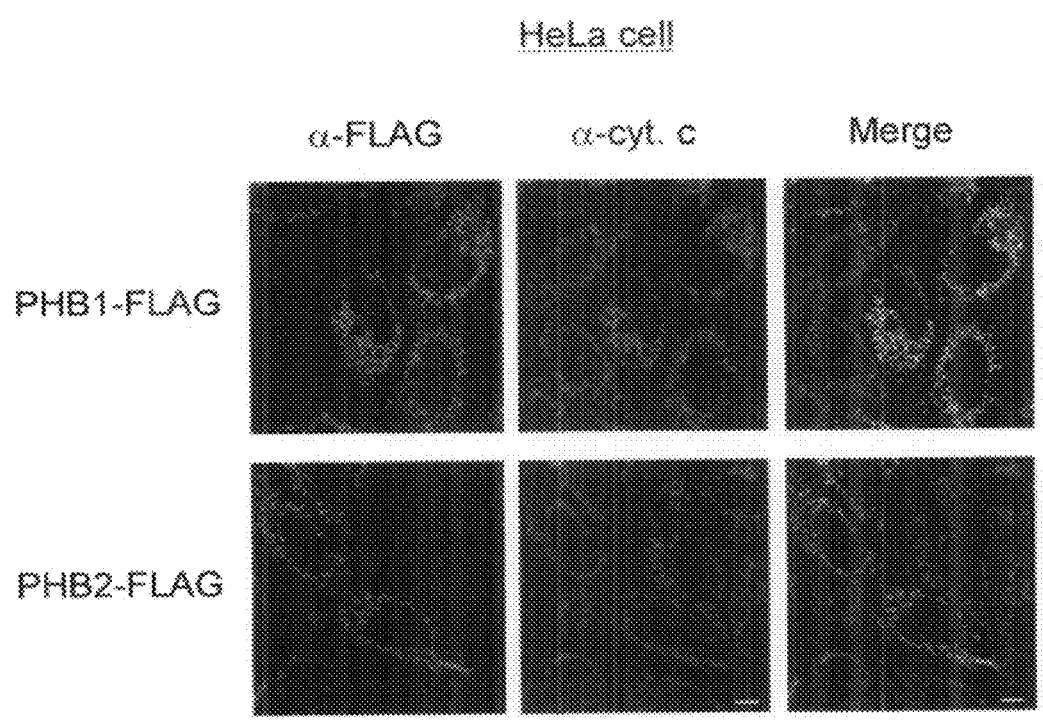
FIG. 1 shows confocal laser scanning micrographs showing HeLa cells expressing PHB1-FLAG or PHB2-FLAG in Example 1.

FIG. 1 shows the results. FIG. 1 shows confocal laser scanning micrographs showing HeLa cells expressing PHB1-FLAG or PHB2-FLAG. In FIG. 1, "α-FLAG" denotes images (green) of staining with the anti-FLAG antibody and "α-cyt.c" denotes images (red) of staining with the anti-cytochrome C antibody. Moreover, "Merge" shows merged images of the two.

As shown in FIG. 1, when PHB1-FLAG and PHB2-FLAG were each transiently expressed by HeLa cells, PHB1-FLAG and PHB2-FLAG were found to be localized in mitochondria. PHB1-FLAG and PHB2-FLAG in HeLa cells were found to be co-localized with cyt.c, which is a mitochondria marker.

Example 2

Disappearance of Mitochondrial Membrane Potential by PHB1 Protein or PHB2 Protein Expression As described in Example 1, when PHB1-FLAG and PHB2-FLAG were separately transiently expressed by HeLa cells, PHB1-FLAG and PHB2-FLAG were found to be localized in mitochondria.

HeLa cells expressing PHB1-FLAG or PHB2-FLAG were then stained with Rh123, which is a mitochondrial staining marker, depending on mitochondrial membrane potential. Similarly, a gene encoding a fusion protein (hereinafter, referred to as "SLP2-FLAG") in which a FLAG tag had been fused to the carboxyl terminus of an SLP2, protein (NCBI accession No: NP_038470) (J Biol Chem. 2000 Mar. 17; 275(11): 8062-71) was transiently expressed by HeLa cells, followed by staining with Rh123. Furthermore, as a control, HeLa cells that had not been transfected with any genes were stained with Rh123.

Figure 2:
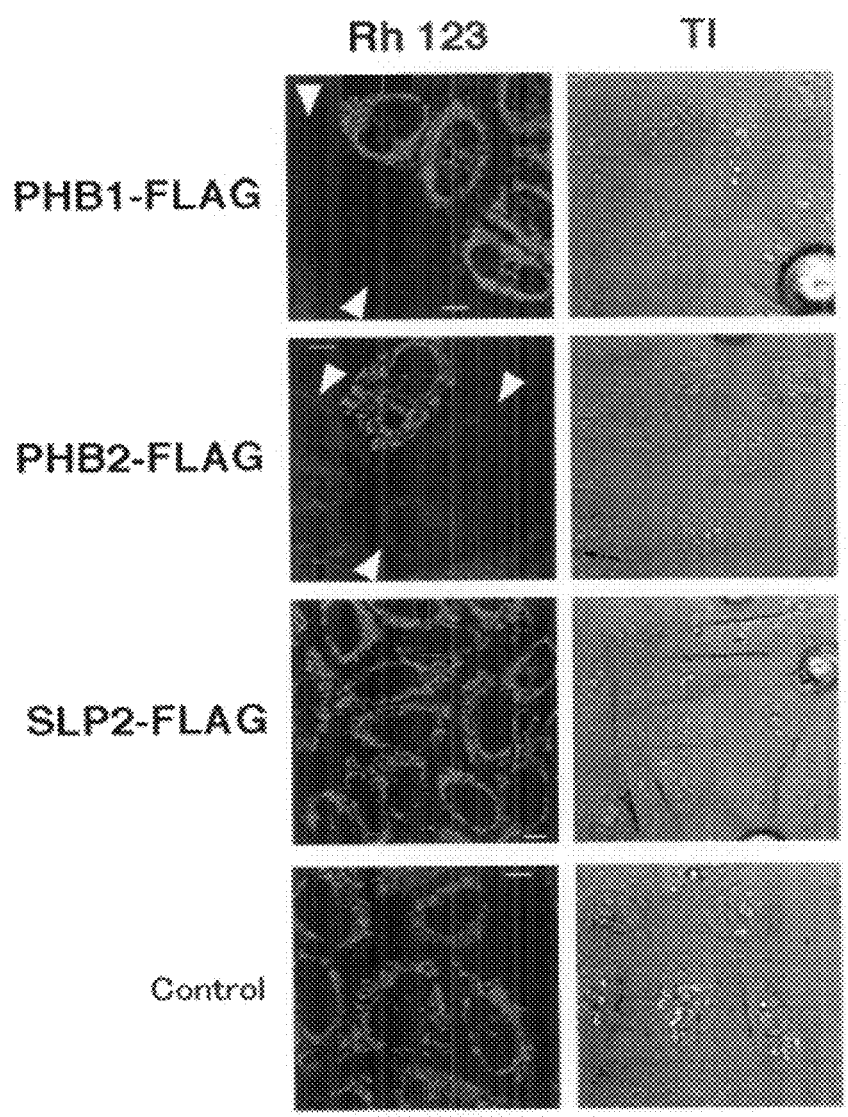
FIG. 2 shows photographs showing HeLa cells expressing each gene, which were stained with Rh123, in Example 2.

FIG. 2 shows the results. FIG. 2 shows photographs showing HeLa cells expressing each gene, such cells having been stained with Rh123. In FIG. 2, "TI" denotes photographs of transmission images,.

As shown in FIG. 2, it was revealed that HeLa cells overexpressing PHB1-FLAG or PHB2-FLAG were not stained with Rh123. This indicates disappearance of mitochondrial membrane potential due to forced expression of PHB1-FLAG or PHB2-FLAG, suggesting possible involvement of the PHB protein in regulation of membrane potential in mitochondria.

Example 3

Molecular Functional Analysis of PHB2 Protein

To elucidate the molecular functions of the PHB2 protein, an interaction factor of the PHB2 protein in mitochondria was searched.

First, immunoprecipitation (IP) analysis and mass spectrometry (MASS analysis) were conducted using purified mitochondrial fractions derived from HeLa cells expressing PHB2-FLAG, which had been prepared in Example 1.

In IP analysis, an immunoprecipitation method was performed using an anti-FLAG antibody, the precipitates were subjected to 12% SDS-PAGE, protein staining was performed, and then proteins that had been co-precipitated with the PHB2-FLAG protein were detected.

Meanwhile, in MASS analysis, the bands of proteins obtained by IP analysis were excised and then subjected to digestion using trypsin within gel, the thus digested peptides were extracted, and then peptide fragments were identified using nanoscale high performance liquid chromatography and tandem mass spectrometer (nano LC-MS/MS). Subsequently, proteins were identified by database analysis.

Figure 3:
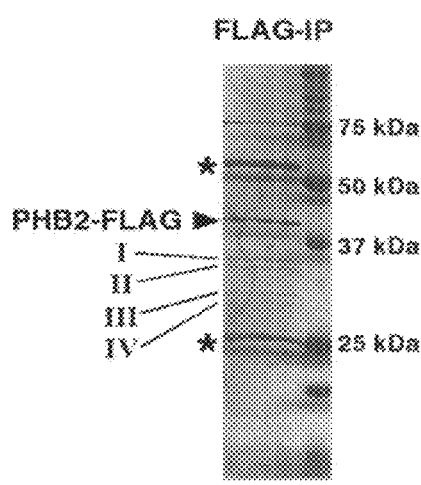
FIG. 3 shows the results of IP analysis and MASS analysis in Example 3.

FIG. 3 shows the results of IP analysis and MASS analysis.

As is understood from FIG. 3, mitochondrial protein Hax-1 (NCBI accession No: NP_006109) having an anti-apoptotic effect, the VDAC2 protein (Swiss-Prot accession No: P45880), which is a configuration factor of PTP (permeability transition pore), an ANT2 protein (NCBI accession No: NP_001143), and the PHB1 protein (NCBI accession No: NP_002625) known to form a complex with the PHB2 protein (Curr. Biol. 7 (8), 607-610 (1997)) were obtained as factors interacting with the PHB2 protein.

Example 4

Interaction Between PHB2 Protein and Hax-1 Protein

Interaction of the PHB2 protein with the Hax-1 protein, the VDAC2 protein, and the PHB1 protein was confirmed via IP analysis described in Example 3 and Western blot analysis using specific antibodies against the PHB2 protein, the Hax-1 protein, the VDAC2 protein, and the PHB1 protein.

Accordingly, interaction between the PHB2 protein and the Hax-1 protein was examined by an in vitro binding experiment.

Methods employed herein are as follows. A glutathione S-transferase (GST)-PHB2 fusion protein (the protein prepared by fusing a GST protein to the N-terminus of the PHB2 protein) that had been synthesized using *Escherichia coli* was mixed in vitro with a PHB1-FLAG protein and a Hax-1-FLAG protein (the protein prepared by:fusing a FLAG tag to the C-terminus of the Hax-1 protein), which had been translated in vitro using a reticulocyte lysate solution. GST fusion proteins were then pulled down using glutathione-sepharose beads, so as to obtain precipitates. Subsequently, the precipitates were subjected to SDS-PAGE and then the Western blot method was performed using an anti-FLAG antibody. Thus, whether or not each FLAG fusion protein had bound to the PHB2 protein was examined.

Figure 4:
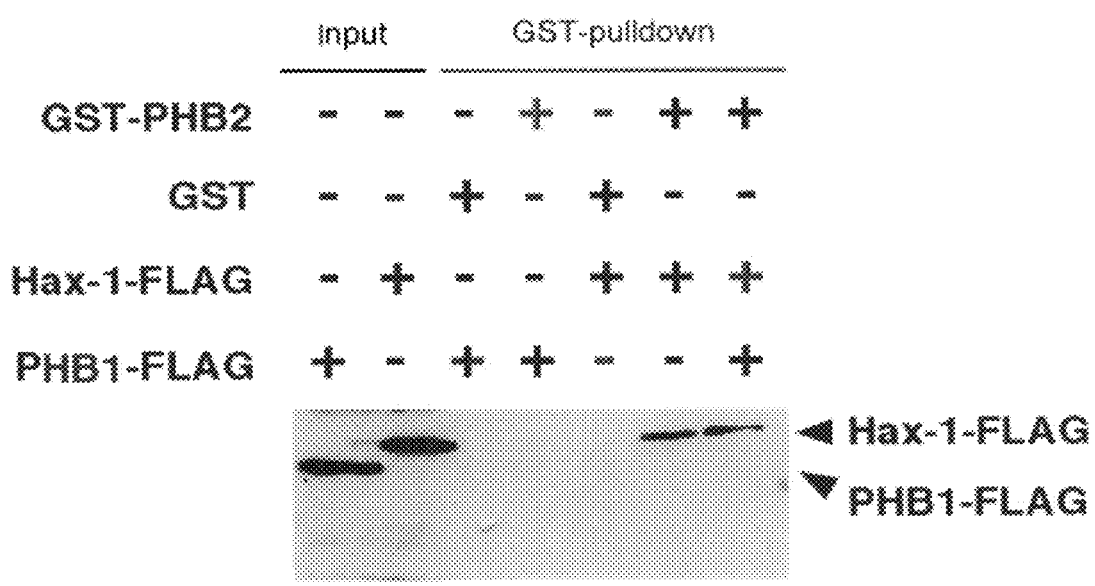
FIG. 4 shows the results of an in vitro binding experiment concerning the interaction between a PHB2 protein and an Hax-1 protein in Example 4.

FIG. 4 shows the results. In FIG. 4, "Input" denotes each FLAG fusion protein mixed therein. Furthermore, "GST-pulldown" denotes a precipitate obtained via precipitation using glutathione-sepharose beads. Furthermore, "−" denotes that the protein was not mixed in the reaction system, "+" denotes that the protein was mixed in the reaction system.

As shown in FIG. 4, it was revealed that the PHB2 protein directly interacts with the Hax-1 protein.

Example 5

PHB2 Knockdown by RNAi Method

PHB2 knockdown was performed in HeLa cells by an RNAi method. siRNA consisting of the nucleotide sequence of SEQ ID NO: 1 was used herein. Furthermore, PHB1 knockdown was also performed using siRNA (SEQ ID NO: 23) for PHB1.

The method employed herein is as follows. A plasmid was constructed by inserting nucleotide sequences for expression of short hairpin RNAs partially matching the cDNA of PHB2 and cDNA of PHB1 into a pScilencer 3.1-H1 puro vector having a puromycin resistance gene. Cultured cells were transfected with the thus prepared plasmids. Subsequently, puromycin was added to medium, so that cells in which target genes had been knocked down could be obtained.

Figure 5:
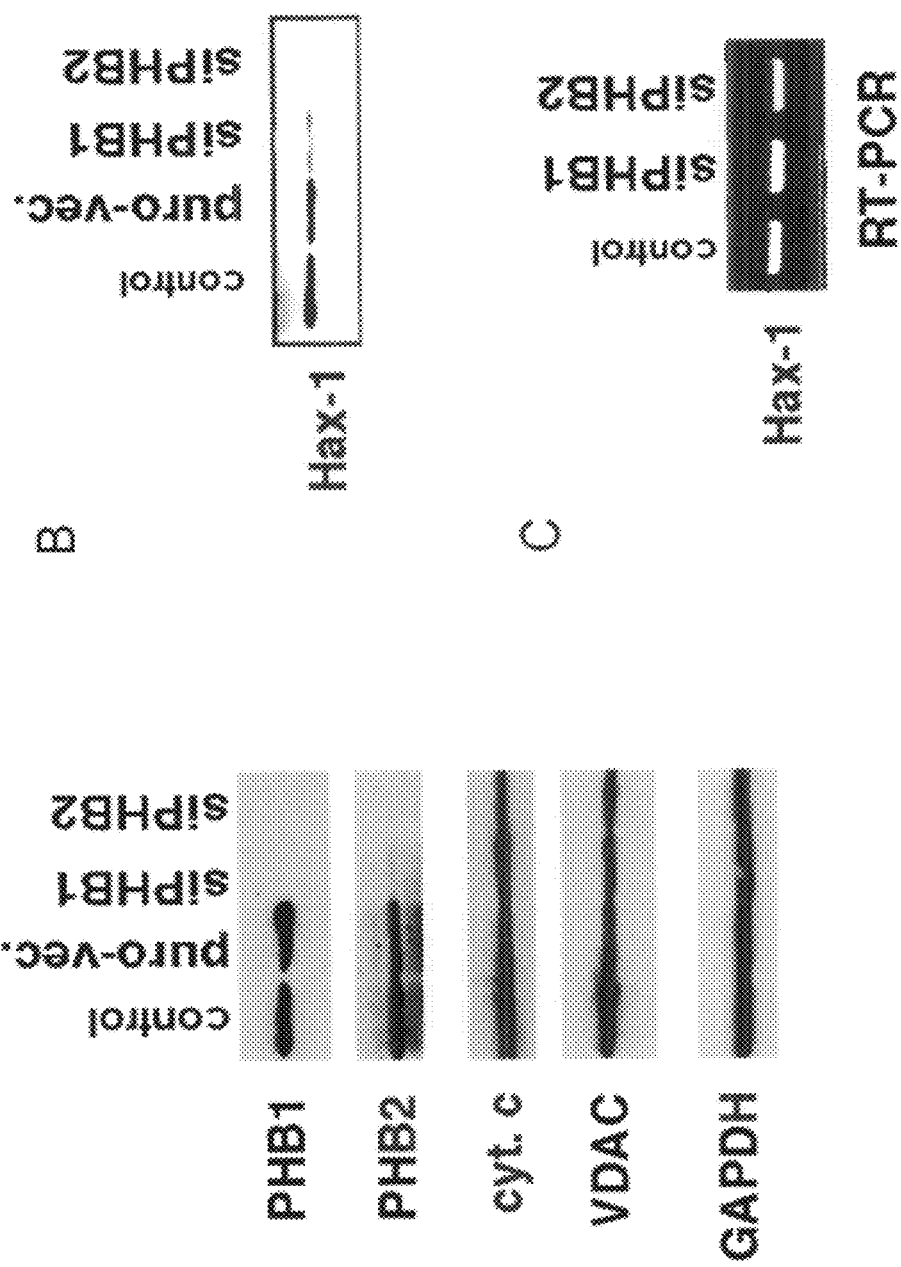
FIG. 5 shows the results of PHB2 knockdown by an RNAi method in Example 5.

FIGS. 5A to C show the results. FIG. 5A shows the results of Western blot analysis using an antibody against each protein when PHB1 knockdown or PHB2 knockdown was performed. FIG. 5B shows the results of Western blot analysis using an antibody against the Hax-1 protein when PHB1 knockdown or PHB2 knockdown was performed. FIG. 5C shows the results of RT-PCR by which the Hax-1 mRNA level was measured when PHB1 knockdown or PHB2 knockdown was performed. In FIGS. 5A to C, "siPHB1" or "siPHB2" indicates the result of PHB1 knockdown or PHB2 knockdown performed by the RNAi method. "Control" denotes cells not transfected with any genes and "puro-vec." denotes cells transfected with a puromycin resistance gene and then subjected to drug selection.

As shown in FIGS. 5A to C, when HeLa cells were subjected to PHB2 knockdown using the RNAi method, the expression levels of the Hax-1 protein and the PHB1 protein, which are interaction factors, were found to be decreased. However, the mRNA of PHB1 and the mRNA of PHB2 were not found to be decreased. It has been reported that yeast PHB interacts with a novel synthesized mitochondrial protein so as to stabilize the protein (Mol. Cell. Biol. 19, 3435-3442 (1999) and EMBO J. 19, 2444-2451 (2000)). Accordingly, it is thought that human PHB2 protein may also stabilize the Hax-1 protein, which is an interaction factor.

Example 6

Decrease in Mitochondrial Membrane Potential and Induction of Caspase-Dependent Cell Death (Apoptosis) in PHB2 Knockdown HeLa Cell In this example, mitochondrial membrane potential and caspase-dependent cell death (apoptosis) in HeLa cells subjected in Example 5 to PHB1 knockdown or PHB2 knockdown were examined.

A method similar to the method employed for knockdown performed in Example 5 was employed.

Figure 6:
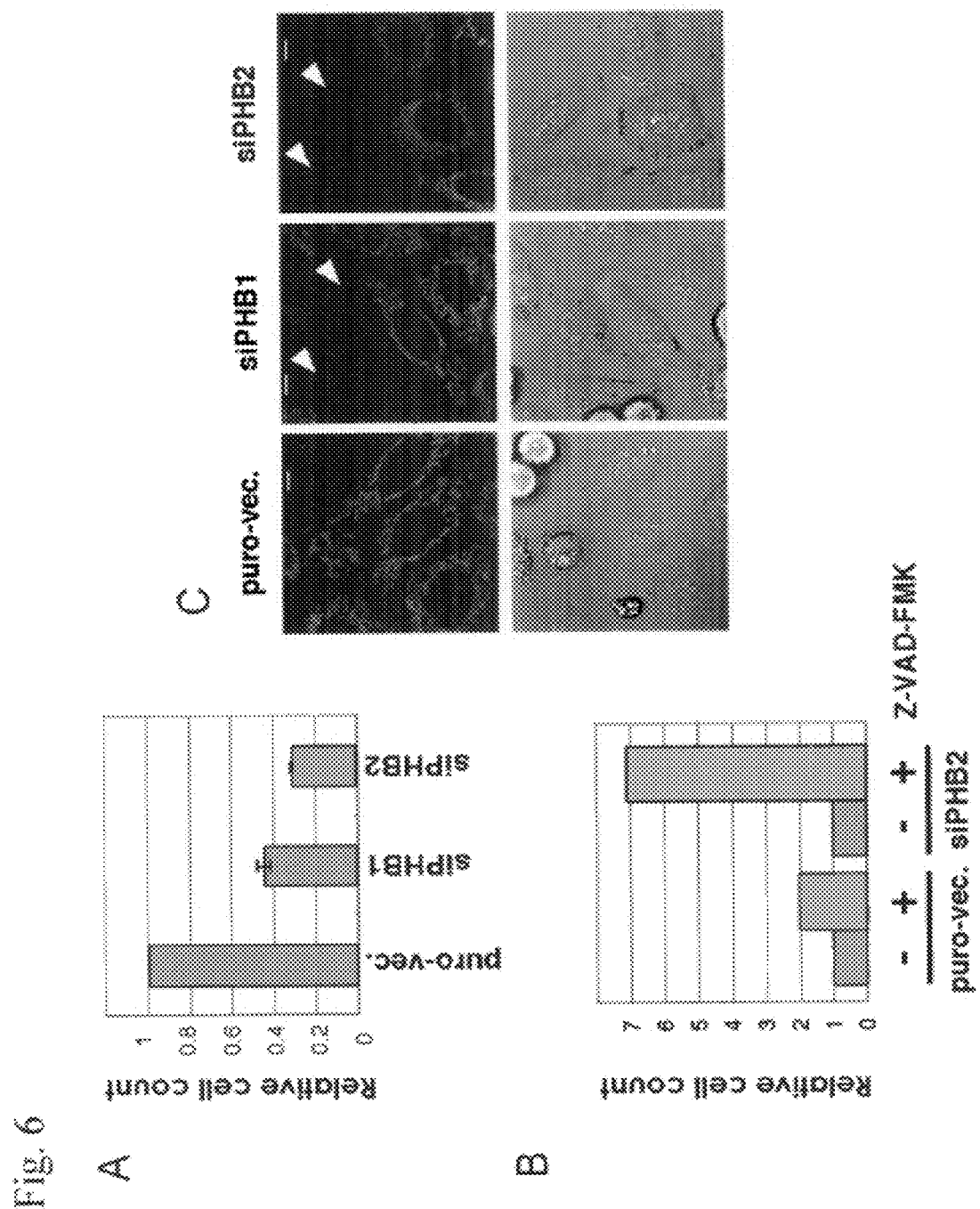
FIG. 6 shows the results of examining mitochondrial membrane potential and caspase-dependent cell death (apoptosis) in HeLa cells that were subjected to PHB1 or PHB2 knockdown in Example 6.

FIGS. 6A to C show the results. FIGS. 6A and B show relative cell counts of HeLa cells subjected to PHB1 knockdown and HeLa cells subjected to PHB2 knockdown. In FIG. 6B, "Z-VAD-FMK" is an inhibitor for the caspase which is activated in apoptosis, and "+" or "−" with reference to Z-VAD-FMK denotes addition or no addition to the medium. FIG. 6C shows the results of Rh123 staining in HeLa cells subjected to PHB1 knockdown or PHB2 knockdown. In FIGS. 6A to C, "siPHB1" or "siPHB2" indicates the result of PHB1 knockdown or PHB2 knockdown by the RNAi method; and "puro-vec." indicates the result of transfection with a plasmid vector having a puromycin resistance gene.

As shown in FIGS. 6A and B, it was revealed that caspase-dependent cell death (apoptosis) had been induced in HeLa cells subjected to PHB1 knockdown or PHB2 knockdown. Moreover, as shown in FIG. 6C, it was revealed that mitochondrial membrane potential had been decreased in some of HeLa cells subjected to PHB1 knockdown or PHB2 knockdown.

Example 7

Hax-1 Knockdown by RNAi Method

In this Example, HeLa cells were subjected to the knockdown of Hax-1, which is an interaction factor of PHB2. siRNA consisting of the nucleotide sequence of SEQ ID NO: 24 was used as siRNA for Hax-1.

The method employed herein is as follows. A plasmid was constructed by inserting a nucleotide sequence for the expression of short hairpin RNA partially matching Hax-1 cDNA into a pScilencer 3.1-H1 puro vector having puromycin resistance gene according to the method of Example 5.

Figure 7:
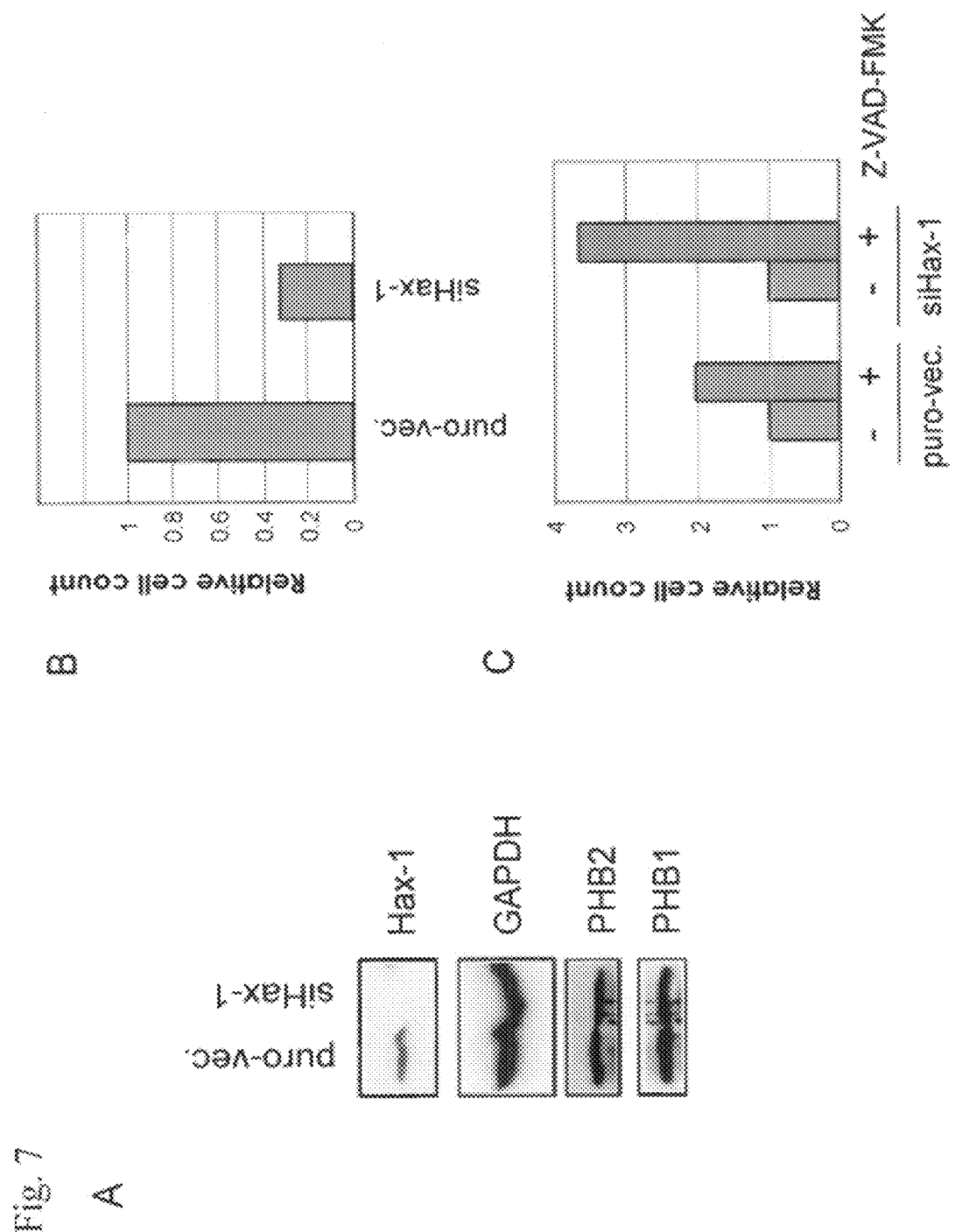
FIG. 7 shows the results of Hax-1 knockdown by an RNAi method in Example 7.

FIGS. 7A to C show the results. FIG. 7A shows the result of Western blot analysis using an antibody against each protein when Hax-1 knockdown was performed. FIGS. 7B and C show relative cell counts of HeLa cells subjected to Hax-1 knockdown. In FIG. 7, "Z-VAD-FMK" and "+" or "−" with reference to Z-VAD-FMK have the same meaning as they do in FIG. 6. In FIGS. 7A to C, "siHax-1" indicates the result of Hax-1 knockdown performed by the RNAi method and "puro-vec." indicates the result of transfection with a plasmid vector having a puromycin resistance gene.

As shown in FIGS. 7A to C, Hax-1 knockdown did not affect the expression levels of the PHB1 protein and the PHB2 protein. However, it induced apoptosis similar to that induced by PHB2 knockdown. Hence, it was thought that a decrease in Hax-1 protein expression level is a cause of apoptosis induced by PHB2 knockdown. Therefore, it was demonstrated that the PHB2 protein exerts its anti-apoptotic effect via maintenance of the expression level of the Hax-1 protein.

Example 8

Change in Mitochondrial Morphology Due to PHB2 Knockdown

In this Example, changes in mitochondrial morphology in HeLa cells subjected to PHB1 knockdown, PHB2 knockdown, or Hax-1 knockdown described in Examples 5 and 7 were examined.

The method employed herein is as follows. Knockdown cells prepared in Examples 5 and 7 were stained with MitoTracker Red, and then the morphology of mitochondria was observed under a confocal laser scanning microscope.

Figure 8:
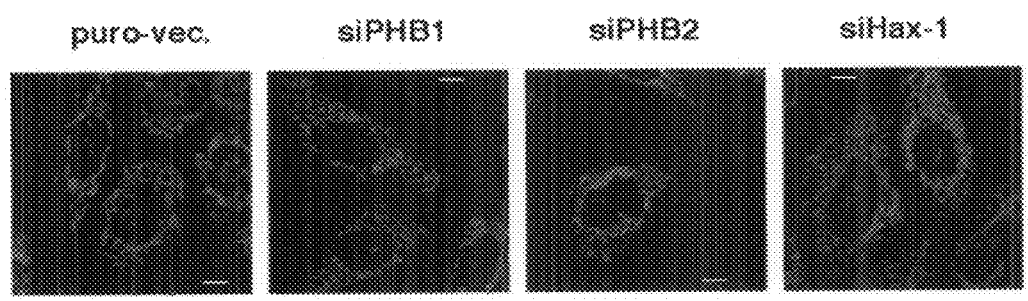
FIG. 8 shows photographs showing PHB1, PHB2, or Hax-1 knockdown cells in which mitochondria were stained with MitoTracker Red in Example 8.

FIG. 8 shows the results. In FIG. 8, "puro-vec." indicates the results of transfection with a plasmid vector having a puromycin resistance gene. Furthermore, "siPHB1," "siPHB2," and "siHax-1" denote the results of subjecting HeLa cells to PHB1 knockdown, PHB2 knockdown, and Hax-1 knockdown, respectively.

As shown in FIG. 8, mitochondrial fragmentation (a change in mitochondrial morphology) was observed in PHB1 or PHB2 knockdown cells in which mitochondria had been stained with MitoTracker Red. Such mitochondrial fragmentation was not observed in Hax-1 knockdown cells. Hence, this mitochondrial fragmentation was thought to take place in a manner specific to PHB protein knockdown and to be the result of a morphological change not mediated by Hax-1.

Furthermore, the above PHB1 knockdown, PHB2 knockdown, or Hax-1 knockdown cells were subjected to Western blot analysis using an antibody against an OPA1 protein, which is a mitochondrial fusion factor.

The method employed herein is as follows. A cell extract was prepared from each type of knockdown cell and then subjected to the Western blot method. An anti-OPA1 polyclonal rabbit antibody was used as a primary antibody.

Figure 9:
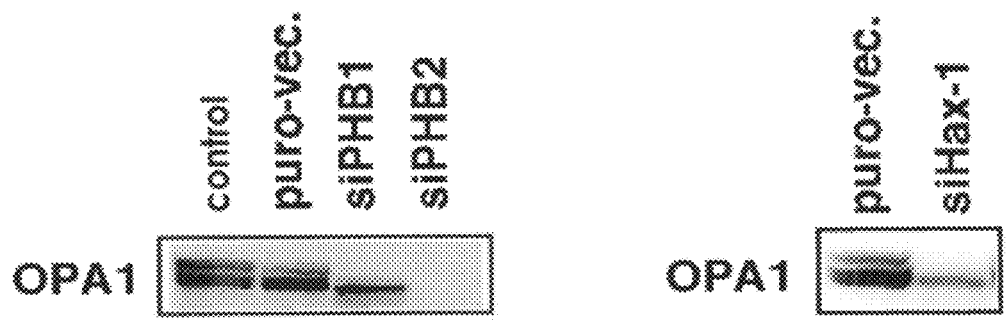
FIG. 9 shows the results of Western blot analysis using an antibody against an OPA1 protein in Example 8.

FIG. 9 shows the results. In FIG. 9, "control" denotes untransfected cells. Moreover, "puro-vec.," "siPHB1," "siPHB2," and "siHax-1" indicate the results of cells similar to FIG. 8.

As shown in FIG. 9, a significantly decreased expression level of the OPA1 protein was observed in PHB2 knockdown cells. Hence, it was concluded that mitochondrial fragmentation due to a decrease in OPA1 protein level had taken place. On the other hand, the OPA1 protein level was also found to be decreased in Hax-1 knockdown cells. Moreover, a decrease in OPA1 protein expression level due to PHB1 knockdown was not significant compared with the same due to PHB2 knockdown, but mitochondrial fragmentation was induced to a degree equivalent to that induced by PHB2 knockdown (FIG. 8).

It is known that the OPA1 protein maintains mitochondrial morphology through a balance with other factors (e.g., Drp1) for regulating mitochondrial morphology (Cell. 2004 Dec. 17; 119 (6): 873-87). Mitochondrial fragmentation in PHB1 knockdown cells is thought to be associated with some factors other than the OPA1 expression level.

Example 9

Intracellular Localization of PHB1 Protein or PHB2 Protein in MCF-7 Cell

As shown in Example 1, the PHB1 protein and the PHB2 protein were localized in mitochondria of HeLa cells.

In this Example, intracellular localization of the PHB1 protein and the PHB2 protein in MCF-7 cells (derived from human breast cancer) was examined, in addition to that in HeLa cells (derived from human cervical cancer).

The method employed herein is as follows. A mammalian cell expression vector was constructed by ligating cDNA encoding the PHB2 or PHB1 protein (fusion proteins are referred to as "PHB2-GFP" and "PHB1-GFP," respectively) in which a green fluorescent protein (GFP) had been ligated to the C-terminus. Cultured cells were then transfected with the vector, following which the intracellular localization of the GFP fusion proteins was observed under a confocal laser scanning microscope.

Figure 10:
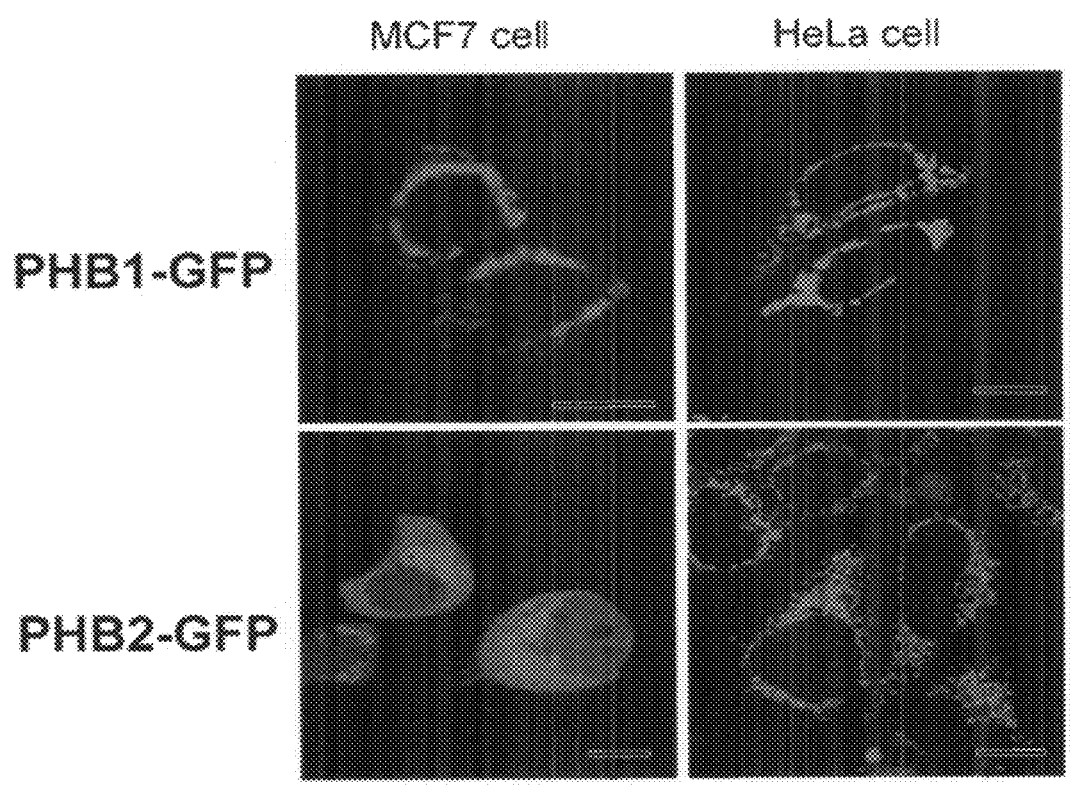
FIG. 10 shows micrographs showing MCF-7 cells and HeLa cells expressing PHB1-GFP or PHB2-GFP in Example 9.

FIG. 10 shows the results. FIG. 10 shows micrographs showing MCF-7 cells expressing PHB1-GFP or PHB2-GFP and HeLa cells expressing PHB1-GFP or PHB2-GFP. As shown in FIG. 10, when MCF-7 cells and HeLa cells were transfected with a gene encoding PHB1-GFP, PHB1-GFP was found to be localized in mitochondria in both types of cells. On the other hand, PHB2-GFP was found to be localized in the mitochondria of HeLa cells, but in the case of MCF-7 cells, some PHB2-GFPs were also found to be localized in the nucleus.

Example 10

Interaction Between PHB2 Protein and Nuclear Receptor ERα

In this Example, interaction between the PHB2 protein and a nuclear receptor ERα was examined.

The method employed herein is as follows. HeLa cells were transfected with an ERα gene and a PHB2-GFP gene incorporated in an expression vector. Subsequently, the cells were fixed and then cell immunostaining was performed using an anti-ERα rabbit polyclonal antibody as a primary antibody and a Cy3-labeled anti-rabbit antibody as a secondary antibody.

Figure 11:
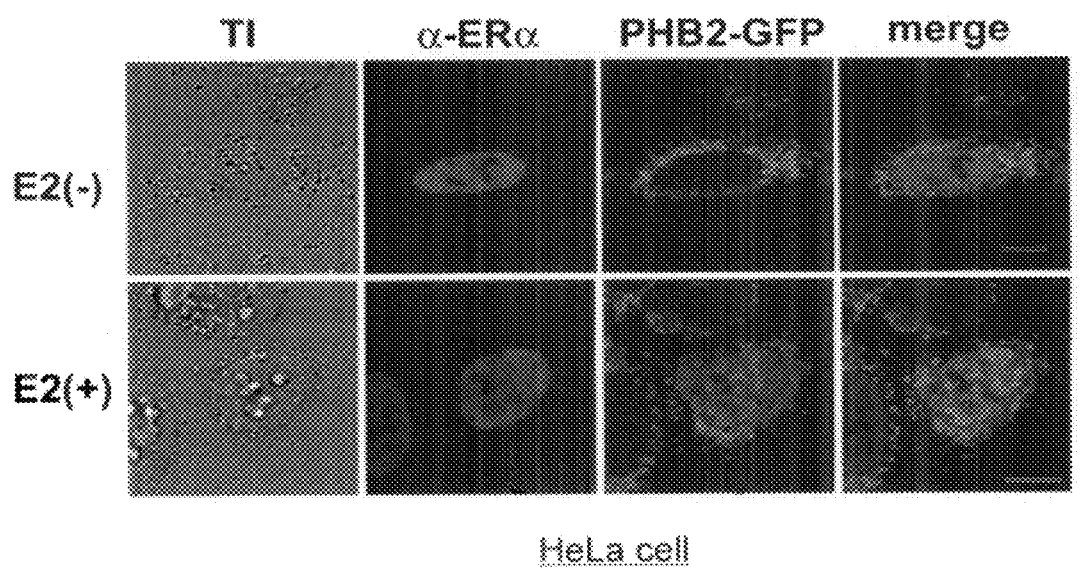
FIG. 11 shows confocal laser scanning micrographs showing HeLa cells that were caused to coexpress PHB2-GFP and ERα in Example 10.

FIG. 11 shows the results. FIG. 11 shows confocal laser scanning micrographs obtained when PHB2-GFP and ERα had been co-expressed by HeLa cells. In FIG. 11, "TI" denotes transmission images and "a-ERα" denotes anti-ERα antibody-stained images (red). Furthermore, "PHB2-GFP" denotes GFP images (green), and "merge" denotes merged images. "E2(−)" denotes cells cultured in the absence of E2 and "E2(+)" denotes cells cultured in the presence of E2.

As shown in FIG. 11, co-expression of PHB2-GFP with ERα in HeLa cells caused PHB2-GFP to be localized in the nucleus in the presence of E2. It is known based on a previous report that the PHB2 protein binds to the nuclear receptor ERα (J. Biol. Chem. Vol. 275, No. 46, pp. 35848-35856, 2000). Therefore, it was considered that PHB2 binds to ERα in an E2-dependent manner, so as to translocate to the nucleus.

Example 11

Structural Analysis of PHB2 Protein

As shown in the above Example, it was revealed that the PHB2 protein is localized in mitochondria and the nucleus. To elucidate the mechanism, deletion mutants of the PHB2 protein, a chimeric protein having the C-terminus of the PHB2 protein, and the like were prepared. Similarly, a deletion mutant of the PHB1 protein was prepared.

Figure 12:
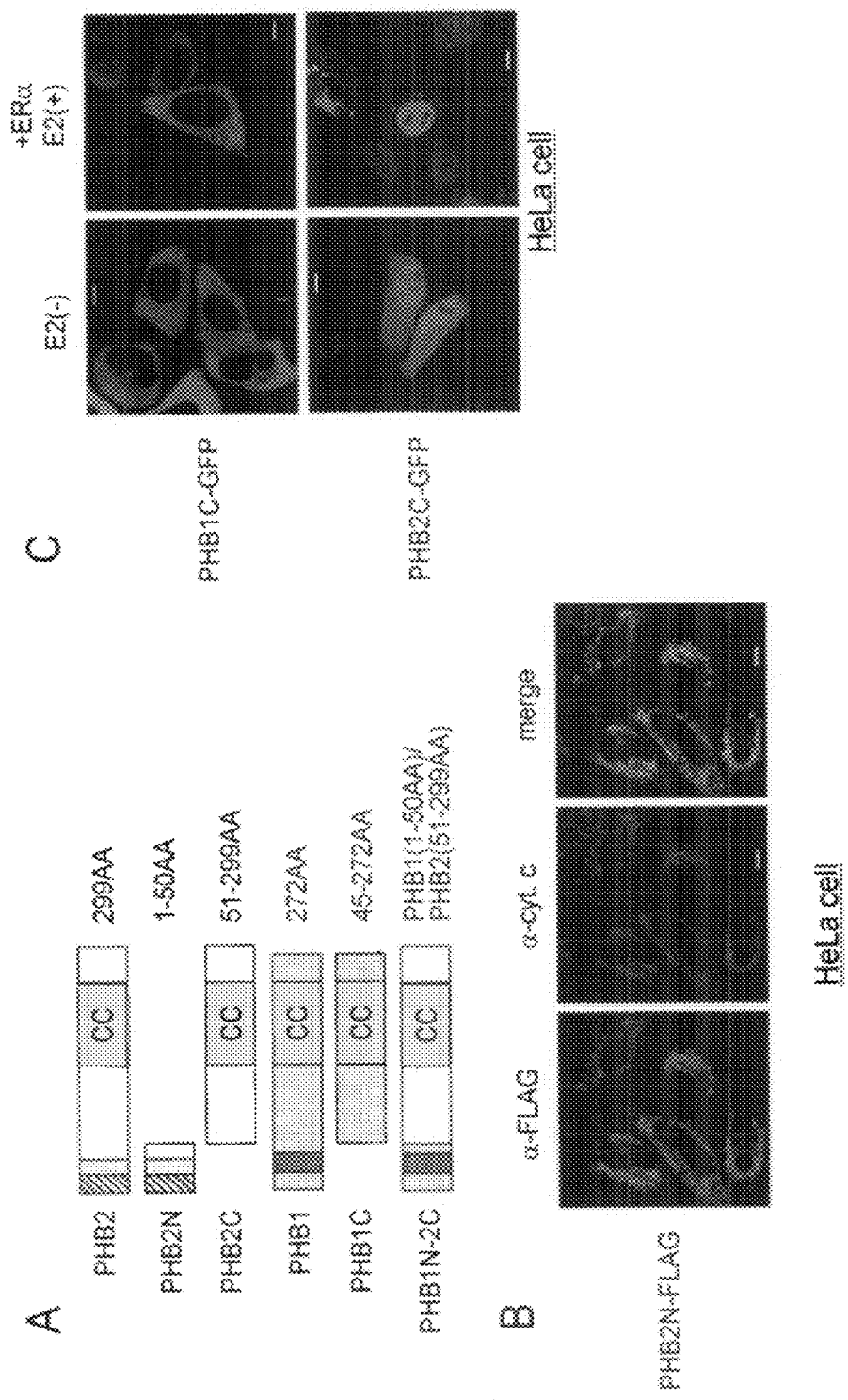
FIG. 12 shows the results of structural analysis of PHB2 proteins in Example 11.
Figure 12:
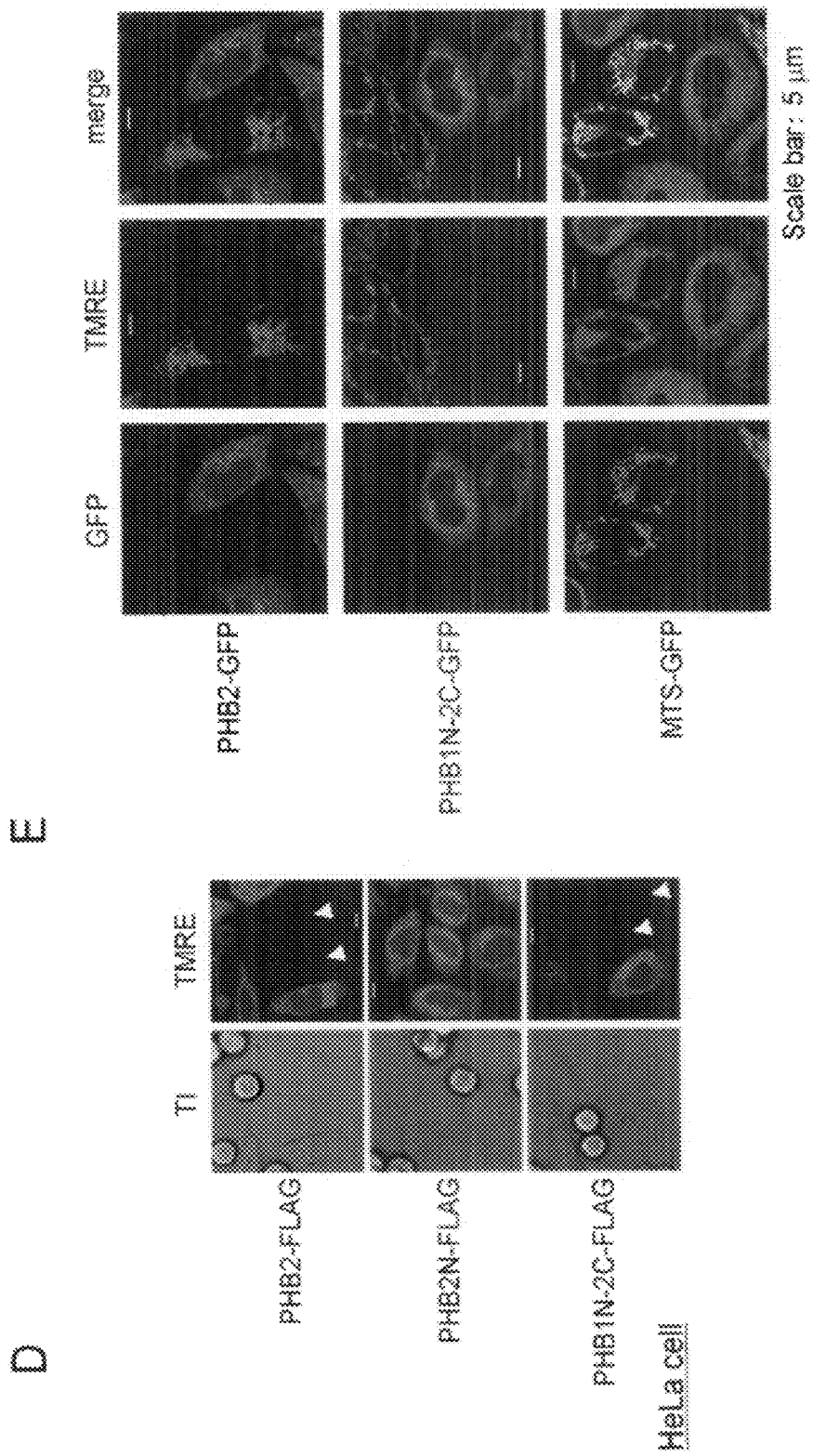

FIG. 12A shows the prepared deletion mutants of the PHB2 protein, the chimeric protein, and the deletion mutant of the PHB1 protein. "PHB2N" is a deletion mutant consisting of the amino acid residues 1 to 50 from the N-terminus of the PHB2 protein. "PHB2C" is a deletion mutant consisting of the amino acid residues 51 to 299 from the N-terminus of the PHB2 protein. Furthermore, "PHB1 C" is a deletion mutant consisting of the amino acid residues 45 to 272 from the N-terminus of the PHB1 protein. Furthermore, a chimeric protein "PHB1N-2C" is a mutant prepared by ligating the amino acid residues 1 to 50 from the N-terminus of the PHB1 protein (having a signal for localization within the inner membrane) to the amino acid residues 51 to 299 from the N-terminus of the PHB2 protein. In FIG. 12A, "cc" denotes a coiled-coil domain.

The method employed herein for preparing a gene encoding such a deletion mutant is as follows. Primers complementary to arbitrary nucleotide portions were prepared, an arbitrary region was amplified by PCR, and then resultant was incorporated into an expression vector, so as to construct an expression vector containing a gene encoding each mutant.

FIGS. 12B to D show the results.

FIG. 12B shows the results of cell immunostaining using HeLa cells expressing a PHB2N-FLAG (the protein prepared by fusing a FLAG tag to the C-terminus of the PHB2N protein). In FIG. 12B, "α-FLAG" denotes an image of staining with an anti-FLAG antibody and "α-cyt.c" denotes an image of staining with an anti-cytochrome C antibody. Furthermore, "merge" denotes a merged image.

FIG. 12C shows intracellular localization of PHB1C-GFP (the protein prepared by fusing a GFP protein to the C-terminus of the PHB1C protein) or PHB2C-GFP (the protein prepared by fusing a GFP protein to the C-terminus of the PHB2C protein) in HeLa cells. "E2(−)" denotes HeLa cells cultured in the absence of E2 and "+Elta E2(+)" denotes ERα-expressing HeLa cells cultured in the presence of E2.

Furthermore, FIG. 12D shows the results of examining the effects of full-length PHB2 (PHB2-FLAG), the PHB2N terminus (PHB2N-FLAG), and the PHB1N-2C chimeric protein (PHB1N-2C-FLAG) on mitochondrial membrane potential in HeLa cells. Each expressed protein is a fusion protein having a FLAG tag on the C-terminus. In addition, detection of mitochondrial membrane potential was performed via staining with the use of TMRE for staining of mitochondria depending on membrane potential. In FIG. 12D, "TI" denotes transmission images.

As shown in FIG. 12B, the PHB2N-FLAG was expressed in mitochondria. Hence, the presence of a mitochondrial targeting signal in the amino terminus of the PHB2 protein was revealed. In the PHB2 protein and the PHB2N protein in FIG. 12A, each box shown with oblique lines denotes the mitochondrial targeting signal, and a box adjacent thereto denotes a transmembrane domain.

Furthermore, as shown in FIG. 12C, PHB2C-GFP translocated to the nucleus in the presence of E2. Hence, the presence of an E2-dependent nuclear translocation signal in the carboxyl terminus of the PHB2 protein was revealed. On the other hand, PHB1 C-GFP did not translocate to the nucleus, even in the presence of E2. Hence, it was revealed that a nuclear translocation signal was absent on the carboxyl terminus of the PHB1 protein and that the signal (or nuclear translocation function) was specific to the PHB2 protein.

Furthermore, as shown in FIG. 12D, it was revealed that the chimeric protein (PHB1N-2C-FLAG) of the C-terminus of PHB2 regulates mitochondrial membrane potential. When transfection was performed with a gene encoding a chimeric protein prepared by fusing the C-terminus of PHB2 to the N-terminus containing PHB1 mitochondrial targeting signal and a transmembrane domain, no changes were observed in mitochondrial functions in the case of the PHB2 N-terminus alone (PHB2N-FLAG). However, mitochondrial membrane potential was revealed to decrease in a manner similar to that in the case of PHB2 as a result of expression of the above chimeric protein. In addition, decreased membrane potential was not observed in the case of the C-terminus alone of PHB1 or the C-terminus alone of PHB2.

Furthermore, it was confirmed by the following experiment that the chimeric protein of the C-terminus of PHB2 causes disappearance of mitochondrial membrane potential.

PHB2-GFP as a positive control (the protein prepared by fusing a GFP protein to the C-terminus of the full-length PHB2 protein), MTS-GFP as a negative control (the protein prepared by fusing a GFP protein to the C-terminus of the mitochondrial targeting signal (MTS) of another protein (human cytochrome C oxidase subunit 8A, 1-29a.a. (NP_004065)), and PHB1N-2C-GFP (the protein prepared by fusing a GFP protein to the C-terminus of the PHB1N-2C chimeric protein) were each expressed by HeLa cells. The presence or the absence of mitochondrial membrane potential was observed under a confocal laser scanning microscope after staining with TMRE (tetramethylrhodamine ethyl ester).

FIG. 12E shows the results. In FIG. 12E, "GFP" denotes fluorescence images resulting from the GFP protein, "TMRE" denotes TMRE staining images, and "merge" denotes merged images.

As shown in FIG. 12E, membrane potential decreased significantly in cells expressing the positive control and the chimeric protein (PHB1N-2C-GFP). However, no decrease in membrane potential was observed in mitochondria expressing the negative control. Specifically, the PHB2 chimeric protein was shown to be an example of an agent for regulating mitochondrial functions.

Example 12

Interaction Between PHB2 Protein and Nuclear Receptor PPARα or PPARγ2

It is considered in Example 10 that PHB2 binds to ERα in an E2-dependent manner so as to translocate to the nucleus.

In this example, interaction between the PHB2 protein and PPARα or PPARγ2, which is a nuclear receptor similar to ERα, was examined.

The method employed herein is as follows. Cells in which a gene encoding PPARα or PPARγ2 and a gene encoding PHB2-GFP or PHB1-GFP incorporated into an expression vector had been co-expressed were observed under a confocal laser scanning microscope.

Figure 13:
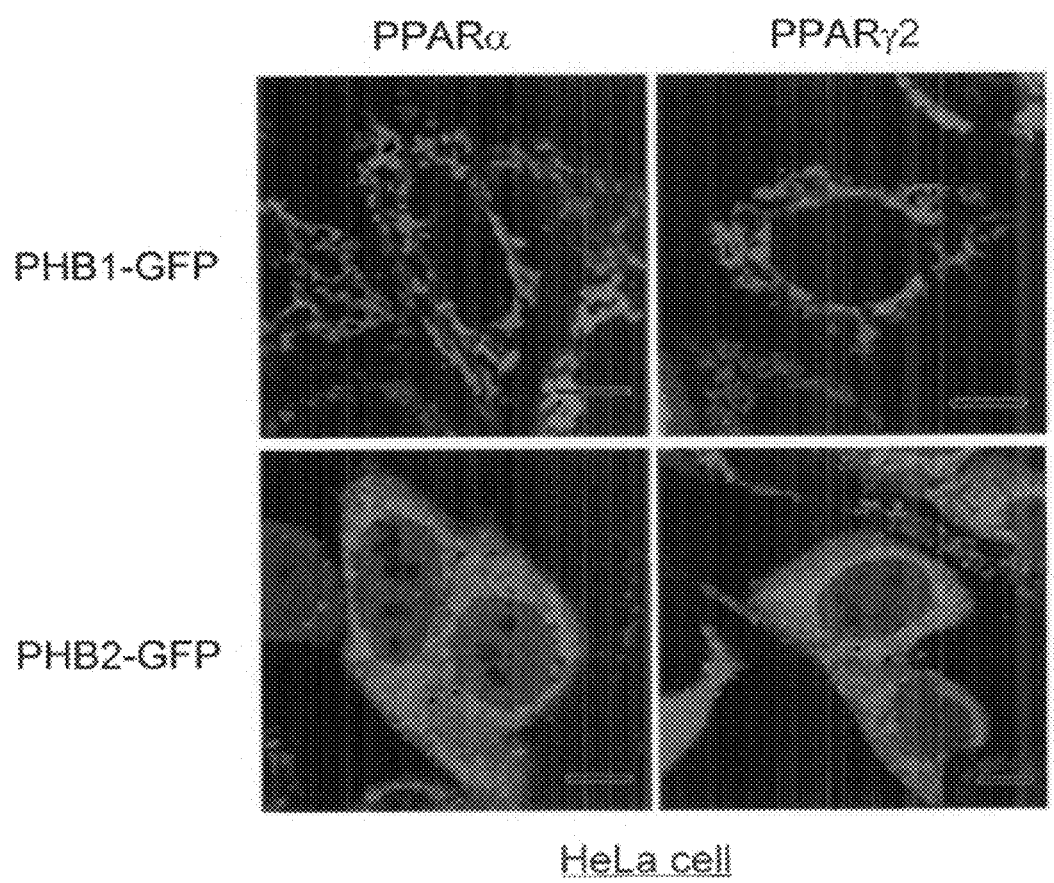
FIG. 13 shows micrographs showing HeLa cells expressing PHB1-GFP or PHB2-GFP and PPARα or PPARγ2 in Example 12.

FIG. 13 shows the results. FIG. 13 shows micrographs of HeLa cells expressing PHB1-GFP or PHB2-GFP and PPARα or PPARγ2. As shown in FIG. 13, it was confirmed in HeLa cells that nuclear translocation of the PHB2 protein takes place in the presence not only of ERα, but also of a similar nuclear receptor, PPARα or PPARγ2, and that the PHB2 protein is specifically localized in the nucleus.

Example 13

Examination of the Transcriptional Repression Activity of the PHB2 Protein

In this example, to examine the transcriptional repression activity of the PHB2 protein, dual luciferase assay was performed using a reporter gene (ERE-Luc) in which a luciferase gene had been ligated downstream of an estrogen-responsive element.

The method employed herein is as follows. HeLa cells were transfected with an ERE-Luc gene and the expression vectors, into each of which an ERα gene, a PHB-2 gene, or a PGC-1α gene had been inserted. Furthermore, transfection with Renilla luciferase having a CMV promoter was simultaneously performed as a control, and then luciferase activity was measured using the luciferase as the internal control.

Figure 14:
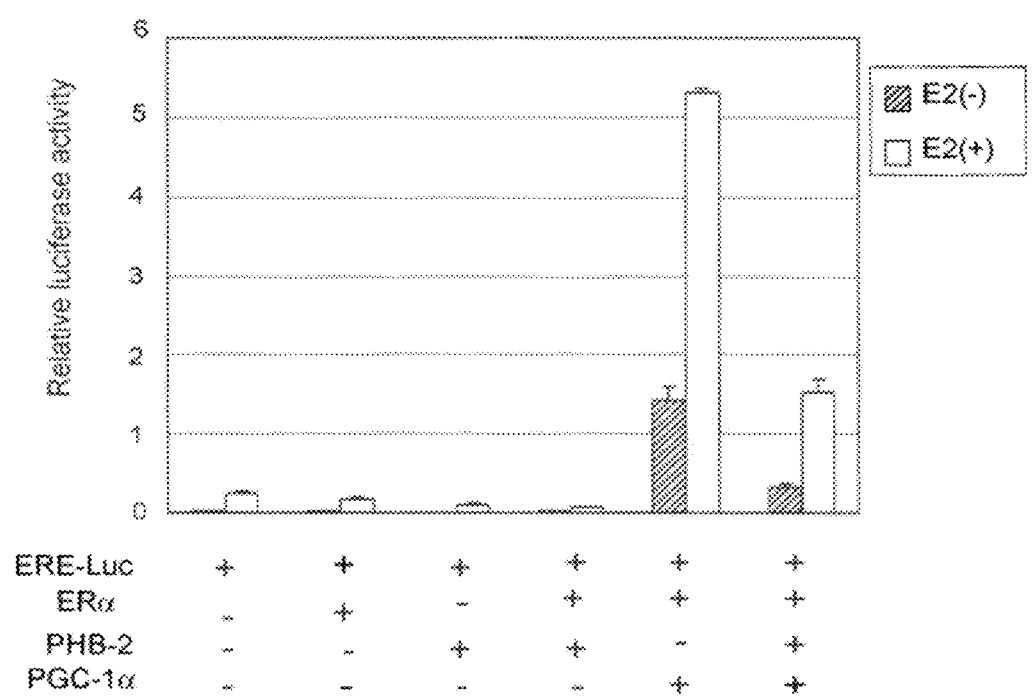
FIG. 14 shows relative luciferase activity in HeLa cells transfected with each gene in Example 13.

FIG. 14 shows the results. FIG. 14 shows the relative luciferase activity in HeLa cells transfected with each gene. "E2(−)" denotes cells cultured in the absence of E2 and "E2 (+)" denotes cells cultured in the presence of E2. In FIG. 14, "+" or "−" denotes the presence or the absence of transfection with each gene. In addition, in FIG. 14, each bar indicates 1SD (standard deviation) and the average value of the values obtained by the experiment that had been conducted independently 3 times.

As shown in FIG. 14, transfection of HeLa cells with the ERα gene and the PGC-1α gene, which is a coactivator of ERα, resulted in enhanced transcriptional activity, and it further enhanced transcriptional activity particularly in the presence of E2. When the PHB2 protein was co-expressed in the HeLa cells with the ERα gene and the PGC-1α gene, a transcriptional-activity-repressing effect could be detected. Therefore, it was revealed that the PHB2 protein functions for transcriptional regulation of the PGC-1α protein, which is a coactivator of ERα, in a repressive manner.

Industrial Applicability

According to the present invention, a PHB2 gene regulator, a therapeutic drug for mitochondrial-function-related disease, and an agent for regulating mitochondrial functions can be provided. Moreover, according to the present invention, a mitochondrial-function-related disease can be detected.

All publications, patents, and patent applications cited herein are incorporated herein by reference in their entirety.

The invention claimed is:

1. A method for screening for an agent for regulating a capability of a PHB2 protein to interact with a protein that is encoded by a gene selected from the group consisting of a VDAC2 gene, a Hax-1 gene, an ANT2 gene and an OPA1 gene, the method comprising:
contacting cells expressing a PHB2 gene with a candidate substance by adding the candidate substance to a culture comprising the cells; and
determining that the candidate substance is the agent for regulating the capability of the PHB2 protein to interact with the protein that is encoded by the gene selected from the group consisting of the VDAC2 gene, the Hax-1 gene, the ANT2 gene and the OPA1 gene if the candidate substance regulates the capability of the PHB2 protein to interact with the protein that is encoded by the gene selected from the group consisting of the VDAC2 gene, the Hax-1 gene, the ANT2 gene and the OPA1 gene in the cells expressing the PHB2 gene caused to come into contact with the candidate substance, when the cells are compared with cells expressing the PHB2 gene in the absence of the candidate substance.

2. The method according to claim 1, wherein the capability to interact is the capability to form a complex.

* * * * *